US 6,555,706 B2

(12) United States Patent
Berk et al.

(10) Patent No.: US 6,555,706 B2
(45) Date of Patent: Apr. 29, 2003

(54) PROCESS FOR MAKING IMINODIACETIC ACID COMPOUNDS FROM MONOETHANOLAMINE SUBSTRATES

(75) Inventors: Howard C. Berk, St. Louis, MO (US); Thaddeus S. Franczyk, II, Chesterfield, MO (US); Robert B. Weisenfeld, Chesterfield, MO (US); David A. Morgenstern, Creve Coeur, MO (US); Juan P. Arhancet, Creve Coeur, MO (US); William L. Moench, St. Louis, MO (US); James C. Peterson, Manchester, MO (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/858,117

(22) Filed: May 15, 2001

(65) Prior Publication Data

US 2002/0019565 A1 Feb. 14, 2002

Related U.S. Application Data

(60) Provisional application No. 60/204,168, filed on May 15, 2000.

(51) Int. Cl.$^7$ .................. C07C 51/16; C07C 229/00; C07C 255/00
(52) U.S. Cl. .................. 562/526; 562/568; 562/553; 562/572; 558/441
(58) Field of Search .................. 562/553, 568, 562/572, 526; 558/441

(56) References Cited

U.S. PATENT DOCUMENTS

| 1,972,465 A | 9/1934 | Ulrich et al. |
| 2,169,736 A | 8/1939 | Kern |
| 2,384,817 A | 9/1945 | Chitwood |
| 3,799,758 A | 3/1974 | Franz |
| 3,950,402 A | 4/1976 | Franz |

(List continued on next page.)

FOREIGN PATENT DOCUMENTS

| DE | 564 787 | 11/1932 |
| DE | 2713374 | 1/1981 |
| JP | 46040611 | 12/1971 |
| JP | 55007252 | 1/1980 |
| WO | WO 92/06069 | 4/1992 |
| WO | WO 94/24091 | 10/1994 |
| WO | WO 97/21669 | 6/1997 |
| WO | WO 99/43430 | 9/1999 |
| WO | WO 00/15601 | 3/2000 |

OTHER PUBLICATIONS

A.I. Kipriyanov and G.I. Kipriyanov, Synthesis of Alcamino Acids by the Cyanohydrin Method, *Chemical Abstracts*, 1933, vol. 27, No. 7, Columbus, Ohio.

(List continued on next page.)

*Primary Examiner*—Samuel Barts
*Assistant Examiner*—Paul A. Zucker
(74) *Attorney, Agent, or Firm*—Senniger, Powers, Leavitt & Roedel

(57) ABSTRACT

This invention is directed to a process for making an iminodiacetic acid compound from a monoethanolamine substrate having the formula:

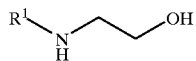

wherein $R^1$ is hydrogen, hydrocarbyl, or substituted hydrocarbyl. The process includes a series of reactions comprising a cyanomethylation, a hydrolysis and a dehydrogenation with the hydrolysis and dehydrogenation steps being carried out either sequentially or concurrently. In a particular embodiment, the iminodiacetic acid produced is disodium iminodiacetic acid and the monoethanolamine substrate used is 2-aminoethanol.

128 Claims, 2 Drawing Sheets

U.S. PATENT DOCUMENTS

| | | | |
|---|---|---|---|
| 3,969,398 A | 7/1976 | Hershman | |
| 4,582,650 A | 4/1986 | Felthouse | |
| 4,624,937 A | 11/1986 | Chou | |
| 4,696,772 A | 9/1987 | Chou | |
| 4,775,498 A | 10/1988 | Gentilcore | |
| 4,782,183 A | 11/1988 | Goto et al. | |
| 5,179,228 A | 1/1993 | Ramon et al. | |
| 5,225,592 A | 7/1993 | Gomez et al. | |
| 5,292,936 A | 3/1994 | Franczyk | |
| 5,367,112 A | 11/1994 | Franczyk | |
| 5,627,125 A | 5/1997 | Ebner et al. | |
| 5,739,390 A | 4/1998 | Franczyk et al. | |
| 5,817,613 A | * 10/1998 | Athey et al. | |
| 6,159,894 A | * 12/2000 | Eisenhuth et al. | |

OTHER PUBLICATIONS

Tsutomu Nakao, et al., Iminodacetic Acid, *Chemical Abstracts*, 1980, vol. 93, No. 11, Columbus, Ohio.

Seiichi Sano, Carboxymethylation of Aminoacetic Acid or of Iminodiacetic Acid, *Chemical Abstracts*, 1972, vol. 76, No. 9, Columbus, Ohio.

International Search Report dated Sep. 10, 2001 from the European Patent Office.

Mark S. Wainwright, Preparation and Utilisation of Raney Copper and Raney Copper–Zinc Catalysts, *Chem. Ind.* (Dekker), 68, 213–30 (1996).

Mark S. Wainwright and Robert B. Anderson, Raney–Nickel–Copper Catalysts, II. Surface and Pore Structures, *Journal of Catalysis*, 1980, p. 124–131.

A.J. Bridgewater, et al., Methanol Synthesis Over Raney Copper–Zinc Catalysts. III. Optimization of Alloy Composition and Catalyst Preparation, *Applied Catalysis*, 1983, p. 369–382.

Robert L. Augustine, Techniques and Applications in Organic Synthesis, *Catalytic Hydrogenation*, 1965, p. 147–149.

John E. Franz, et al., Glyphosate: A Unique Global Herbicide, *ACS Monograph 189*, 233–262.

J.P. Orchard, et al., Preparation and Properties of Raney–Nickel—Cobalt Catalysts, *Journal of Catalysis*, 1983, 189–199.

Kirk–Othmer, *Encyclopedia of Chemical Technology*, Fourth Edition, p. 258, 272 and 291, vol. 16.

A.S. Krisher and O.W. Siebert, *Perry's Chemical Engineers' Handbook*, Sixth Edition, p. 23–42 to 23–49.

Marte Jasik, et al., Technology of IDA Production from Monochloroacetic Acid, *Organika*, 1986, p. 1–8.

Ivan V. Micovic and Milovan D. Ivanoivc, A Modified and Improved Preparation of Iminodiacetonitrile Iminodiacetic Acid and Nitrilotriacetic Acid, *Journal of Serbian Chemical Society*, 1986, p. 435–439.

Eugene Lieber and Fred L. Morritz, The Uses of Raney Nickel, 1953, p. 417–455.

Richard J. Lewis, Sr.,*Hawley's Condensed Chemical Dictionary*, 1997, p. 621 and 955.

D. J. Young, Structure and Leaching Properties, *Journal of Catalysis*, 1980, p. 116–123.

* cited by examiner

PROCESS FOR MAKING IMINODIACETIC ACID COMPOUNDS FROM MONOETHANOLAMINE SUBSTRATES

CROSS-REFERENCE TO RELATED APPLICATIONS

This application claims priority from co-pending U.S. provisional patent application Ser. No. 60/204,168, filed May 15, 2000, which is hereby incorporated herein by reference in its entirety.

FIELD OF THE INVENTION

The present invention relates, in general, to making iminodiacetic compounds from monoethanolamine substrates, and, more particularly, to making iminodiacetic compounds from monoethanolamine substrates through a series of reactions comprising a cyanomethylation, a hydrolysis, and a dehydrogenation.

BACKGROUND OF THE INVENTION

Iminodiacetic acid compounds are useful in various applications. Such compounds (particularly iminodiacetic acid and its salts) are, for example, widely used as raw materials for making pharmaceuticals, agricultural chemicals, and pesticides, and are particularly useful as raw materials for making N-(phosphonomethyl)glycine and its salts. N-(phosphonomethyl)glycine, known in the agricultural chemical industry as "glyphosate," is described by Franz in U.S. Pat. No. 3,799,758. N-(phosphonomethyl)glycine and various salts thereof can be conveniently applied as a post-emergent herbicide in an aqueous formulation, and as a highly effective and commercially important broad-spectrum herbicide useful for killing or controlling the growth of a wide variety of plants, including germinating seeds, emerging seedlings, maturing and established woody and herbaceous vegetation, and aquatic plants. Widely known processes for making N-(phosphonomethyl)glycine and its salts from iminodiacetic acid compounds are disclosed in, for example, Franz, et al., *Glyphosate: A Unique Global Herbicide* (ACS Monograph 189, 1997) at pp. 233–62 (and references cited therein).

Many previously disclosed processes for making iminodiacetic acid compounds convert an intermediate amine compound having at least two identical groups. For example, in U.S. Pat. No. 5,627,125 (and references cited therein), Ebner et al. disclose making disodium iminodiacetate by dehydrogenating two hydroxyethyl groups of N,N-diethanolamine using a strong hydroxide base in the presence of a metallic catalyst. Micovic et al. (*Journal of Serbian Chemical Society*, 51, 435–39 (1986)), on the other hand, describe making iminodiacetonitrile (HN(CH$_2$CN)$_2$), and then hydrolyzing iminodiacetonitrile in acid to form iminodiacetic acid.

Iminodiacetic acid compounds also have been prepared using, for example, processes in which the two carboxymethyl groups are introduced simultaneously. Jasik et al. (*Pol. Organika*, 1–8 (1986)), for example, disclose making iminodiacetic acid and its salts by reacting ammonia with about two equivalents of chloroacetic acid.

Iminodiacetic acid compounds additionally have been made through unsymmetrical chemical intermediates. For example, Sano et al. (Japanese Patent No. 46040611) disclose making iminodiacetic acid and its disodium salt by hydrolyzing N-cyanomethylglycine. Sano et al. report making the N-cyanomethylglycine by reacting glycine with glycolonitrile. Nakao et al. (Japanese Patent No. 55007252) likewise disclose making iminodiacetic acid and its disodium salt by hydrolyzing N-cyanomethylglycine, but Nakao et al. report making the N-cyanomethylglycine by reacting glycine with formaldehyde and an alkali metal cyanide. Sodium glycinate, from which glycine can be obtained readily, may be prepared, for example, by dehydrogenating monoethanolamine. See, e.g., Franczyk et al., U.S. Pat. No. 5,739,390.

A process for making iminodiacetic acid or a salt thereof directly from monoethanolamine substrate is highly desirable. Because mono-, di-, and triethanolamines are all obtained when ammonia is reacted with ethylene oxide in the major commercial production process, monoethanolamine is now more readily available due to the large quantities of diethanolamine utilized commercially to produce disodium iminodiacetate and other materials. Use of monoethanolamine in a process involving a single cyanomethylation to make disodium iminodiacetate would substantially reduce the amount of the highly toxic hydrogen cyanide needed compared to bis-cyanomethylation of ammonia to produce disodium iminodiacetate. Availability of a viable alternative to the current commercial routes could further offer flexibility in the use of existing manufacturing facilities.

Applicants are not aware of any reported processes that directly utilize monoethanolamine to make iminodiacetic acid or salts thereof. Cyanomethylation of monoethanolamine has been disclosed by Athey et al. in PCT application publication number WO 9721669 and Ulrich et al. in U.S. Pat. No. 1,972,465. Chemically, N-cyanomethyl substituted amines are generally unstable, which make their reactivity difficult to predict for new types of reactions or when reactive substituents are present. Athey et al. and Kern (U.S. Pat. No. 2,169,736) report that N-(2-hydroxyethyl)glycine may be formed by alkaline hydrolysis of N-cyanomethylethanolamine in an unreported yield without mentioning any stability problems. Applicants are not, however, aware of any previously reported processes which simultaneously or sequentially convert the cyanomethyl group and the hydroxyethyl group of N-cyanomethylated monoethanolamines to form iminodiacetic compounds.

SUMMARY OF THE INVENTION

This invention generally provides for a well-defined, low-cost process for making iminodiacetic acid compounds (especially iminodiacetic acid and salts thereof) from monoethanolamine substrates.

Briefly, therefore, this invention is directed to a process for making an iminodiacetic acid compound from a monoethanolamine substrate having the following formula:

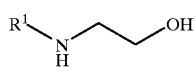

wherein R$^1$ is hydrogen, hydrocarbyl, or substituted hydrocarbyl.

In one embodiment, the process comprises contacting the monoethanolamine substrate with a cyanide source and a formaldehyde source to form a 2-(N-cyanomethylamino)ethanol intermediate. The 2-(N-cyanomethylamino)ethanol intermediate is then contacted with a hydroxide source and a metal-containing catalyst to form the iminodiacetic acid compound.

In another embodiment, the process comprises three steps wherein the monoethanolamine substrate is contacted with a cyanide source and a formaldehyde source to form a 2-(N-cyanomethylamino)ethanol intermediate, the 2-(N-cyanomethylamino)ethanol intermediate is contacted with a hydroxide source to form an N-(2-hydroxyethyl)glycine intermediate, and the N-(2-hydroxyethyl)glycine intermediate is contacted with a metal-containing catalyst to form the iminodiacetic acid compound.

And, in yet another embodiment, the process comprises contacting the monoethanolamine substrate with a metal-containing catalyst to form a glycine intermediate. The glycine intermediate is then contacted with a cyanide source and a formaldehyde source to form an N-cyanomethylglycine intermediate, which is subsequently contacted with a hydroxide source to form the iminodiacetic acid compound.

The present invention is further directed to a process for making an iminodiacetic acid compound from a monoethanolamine substrate. The process comprises continuously or intermittently introducing the monoethanolamine substrate into a cyanomethylation reaction zone wherein the monoethanolamine substrate is contacted with a cyanide source and a formaldehyde source to form a cyanomethylation product comprising an N-cyanomethylated monoethanolamine intermediate. At least a portion of the N-cyanomethylated monoethanolamine intermediate from the cyanomethylation product is then continuously or intermittently introduced into a hydrolysis/dehydrogenation reaction zone wherein the N-cyanomethylated monoethanolamine intermediate is contacted with a hydroxide source and a metal-containing catalyst to form a hydrolysis/dehydrogenation product comprising the iminodiacetic acid compound.

The present invention is further directed to a process for making an iminodiacetic acid compound from a monoethanolamine substrate. The process comprises continuously or intermittently introducing the monoethanolamine substrate into a cyanomethylation reaction zone wherein the monoethanolamine substrate is contacted with a source of formaldehyde and a source of cyanide in the cyanomethylation reaction zone to form a cyanomethylation product comprising a N-cyanomethylated monoethanolamine intermediate. At least a portion of the N-cyanomethylated monoethanolamine intermediate from the cyanomethylation product is continuously or intermittently introduced into a hydrolysis reaction zone wherein the N-cyanomethylated monoethanolamine intermediate is contacted with a hydroxide source to form a hydrolysis product comprising an N-(2-hydroxyethyl)glycine intermediate. At least a portion of the N-(2-hydroxyethyl)glycine intermediate from the hydrolysis product is then continuously or intermittently introduced into a dehydrogenation reaction zone wherein the N-(2-hydroxyethyl)glycine intermediate is contacted with a metal-containing catalyst to form a dehydrogenation product comprising an iminodiacetic acid compound.

The present invention is still further directed to a process for making an iminodiacetic acid compound from a monoethanolamine substrate. The process comprises continuously or intermittently introducing the monoethanolamine substrate into a dehydrogenation reaction zone wherein the monoethanolamine substrate is contacted with a metal-containing catalyst to form a dehydrogenation product comprising a glycine intermediate. At least a portion of the glycine intermediate from the dehydrogenation product is then continuously or intermittently introduced into a cyanomethylation reaction zone and contacted with a cyanide source and a formaldehyde source to form a cyanomethylation product comprising an N-cyanomethylated glycine intermediate. At least a portion of the N-cyanomethylated glycine intermediate from said cyanomethylation product is continuously or intermittently introduced into a hydrolysis reaction zone and contacted with a hydroxide source to form a hydrolysis product comprising an iminodiacetic acid compound.

The present invention is still further directed to a process for making disodium iminodiacetic acid from 2-aminoethanol. The process comprises continuously or intermittently introducing 2-aminoethanol into a cyanomethylation reaction zone wherein the 2-aminoethanol is contacted with a cyanide source and a formaldehyde source to form a cyanomethylation product comprising 2-(N-cyanomethylamino)ethanol. At least a portion of the 2-(N-cyanomethylamino)ethanol from the cyanomethylation product is then continuously or intermittently introduced into a hydrolysis/dehydrogenation reaction zone wherein the 2-(N-cyanomethylamino)ethanol is contacted with a hydroxide source and a metal-containing catalyst to form a hydrolysis/dehydrogenation product comprising disodium iminodiacetic acid.

The present invention is still further directed to a process for making disodium iminodiacetic acid from 2-aminoethanol. The process comprises continuously or intermittently introducing 2-aminoethanol into a cyanomethylation reaction zone for a source of cyanide and a source of formaldehyde to form a cyanomethylation product comprising 2-(N-cyanomethylamino)ethanol. At least a portion of the 2-(N-cyanomethylamino)ethanol from the cyanomethylation product is then continuously or intermittently introduced into a hydrolysis reaction zone, wherein the 2-(N-cyanomethylamino)ethanol is contacted with a hydroxide source to form a hydrolysis product comprising sodium N-(2-hydroxyethyl) glycinate. At least a portion of the sodium N-(2-hydroxyethyl)glycinate from the hydrolysis product is then continuously or intermittently introduced into a dehydrogenation reaction zone and contacted with a metal-containing catalyst to form a dehydrogenation product comprising disodium iminodiacetic acid.

The present invention is still further directed to a process for making disodium iminodiacetic acid from 2-aminoethanol. The process comprises continuously or intermittently introducing 2-aminoethanol into a dehydrogenation reaction zone wherein the 2-aminoethanol is contacted with a metal-containing catalyst to form a dehydrogenation product comprising sodium glycinate. At least a portion of the sodium glycinate from the dehydrogenation product is continuously or intermittently introduced into a cyanomethylation reaction zone and contacted with a cyanide source and a formaldehyde source to form a cyanomethylation product comprising sodium N-cyanomethylglycinate. At least a portion of the sodium N-cyanomethylglycinate from the cyanomethylation product is continuously or intermittently introduced into a hydrolysis reaction zone and contacted with a hydroxide source to form a hydrolysis product comprising disodium iminodiacetic acid.

Other objects and features of this invention will be in part apparent and in part pointed out hereinafter.

DESCRIPTION OF THE PREFERRED EMBODIMENTS

Figure 1:
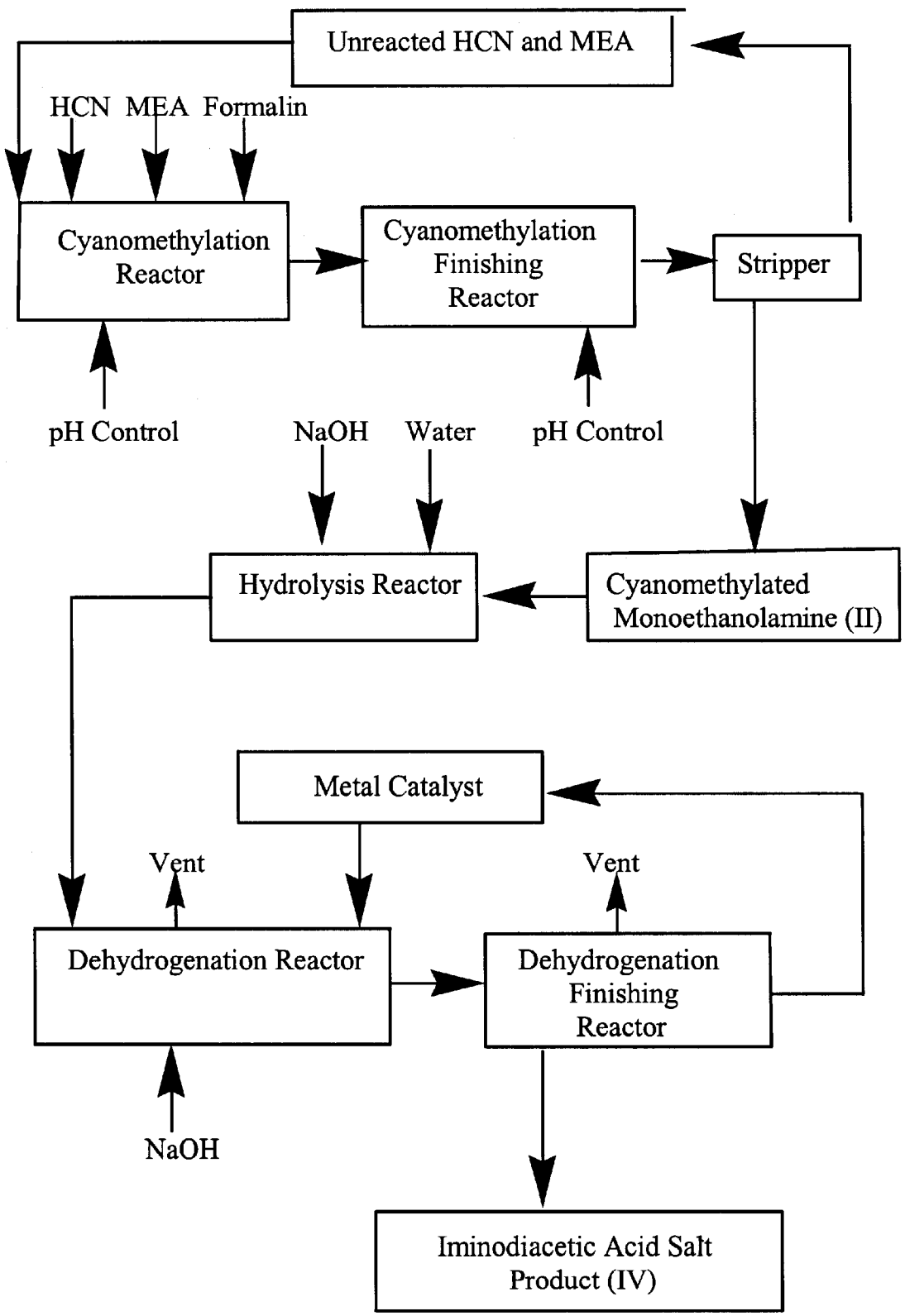
FIG. 1 shows a preferred embodiment for continuously making an iminodiacetic acid salt product from monoethanolamine, wherein the reaction is commenced in a cyanomethylation reaction zone.

The process of the present invention is broadly directed to converting monoaminoethanol substrates to iminodiacetic acid compounds. The monoethanolamine substrate generally has the following formula:

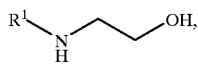

wherein $R^1$ is hydrogen, hydrocarbyl, or substituted hydrocarbyl.

A "hydrocarbyl" may be any group consisting exclusively of carbon and hydrogen. The hydrocarbyl may be branched or unbranched, may be saturated or unsaturated, and may comprise one or more rings. Suitable hydrocarbyl groups include alkyl, alkenyl, alkynyl, and aryl groups. They also include alkyl, alkenyl, alkynyl, and aryl groups substituted with other aliphatic or cyclic hydrocarbyl groups, such as alkaryl, alkenaryl, and alkynaryl. Hydrocarbyls therefore include, for example, methyl, ethyl, propyl, butyl, pentyl, hexyl, octyl, decyl, dodecyl, tetradecyl, hexadecyl, octadecyl, eicosyl, cyclopropyl, cyclobutyl, cyclopentyl, cyclohexyl, methylcyclopentyl, propenyl, butenyl, pentenyl, hexenyl, butynyl, pentynyl, hexynyl, phenyl, naphthyl, anthracenyl, benzyl, and isomers thereof.

A "substituted hydrocarbyl" may be any hydrocarbyl wherein at least one hydrogen atom has been substituted with an atom other than hydrogen or a group of atoms containing at least one atom other than hydrogen (the substituted atom or group preferably is stable in the reaction conditions of the process of the present invention). The hydrogen atom may, for example, be substituted with a halogen atom, such as a chlorine or fluorine atom. The hydrogen atom alternatively may be substituted with an oxygen atom or a group containing an oxygen atom to form, for example, a hydroxy, an ether, an ester, an anhydride, an aldehyde, a ketone, or a carboxylic acid. The hydrogen atom also may be substituted with a group containing a nitrogen atom to form, for example, an amide or a nitro group. Or, for example, the hydrogen atom may be substituted with a group containing a sulfur atom to form, for example, —$SO_3H$.

In one particularly preferred embodiment, $R^1$ is hydrogen. In another particularly preferred embodiment, $R^1$ is hydrocarbyl or substituted hydrocarbyl, and contains from about 1 to about 30 (even more preferably from about 1 to about 20) carbon atoms, with the more preferred hydrocarbyls often being methyl, ethyl, isopropyl, benzyl, and pentyl.

In one embodiment of the present invention, a monoethanolamine substrate is converted into an iminodiacetic acid compound in a process which comprises a cyanomethylation, followed by a hydrolysis and a dehydrogenation. Particularly preferred embodiments of this process are shown in Reaction Scheme 1:

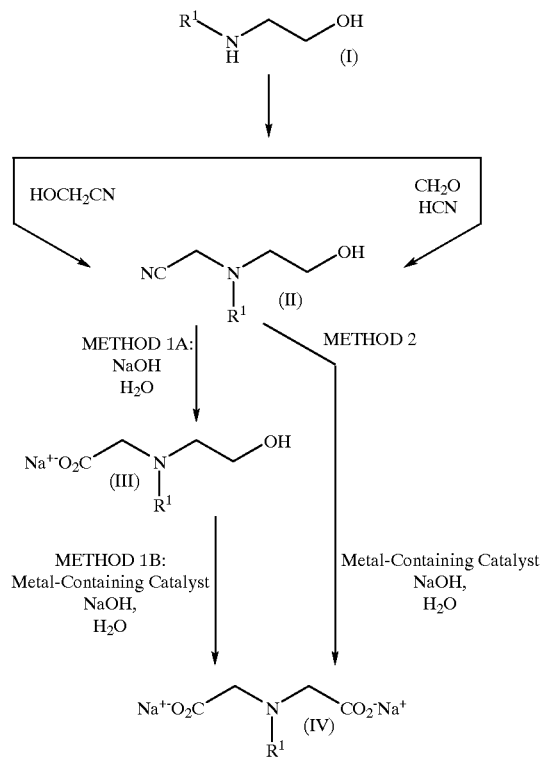

Reaction Scheme 1

As shown in Reaction Scheme 1, the monoethanolamine substrate (I) is cyanomethylated to form an N-cyanomethylated monoethanolamine intermediate (II) by contacting the monoethanolamine substrate (I) with either (a) glycolonitrile ($HOCH_2CN$), or (b) formaldehyde ($CH_2O$) and hydrogen cyanide (HCN). The iminodiacetic acid product (IV) is then formed by either (a) contacting the cyanomethylated monoethanolamine intermediate (II) with a hydroxide source (most preferably NaOH) to hydrolyze the cyanomethylated monoethanolamine intermediate (II) to form an N-(2-hydroxyethyl)glycine intermediate (III) (i.e., Method 1A), and then contacting the N-(2-hydroxyethyl) glycine intermediate (III) with a hydroxide source (most preferably NaOH) and a metal-containing catalyst (most preferably a copper-containing catalyst) to dehydrogenate the N-(2-hydroxyethyl)glycine intermediate (III) (i.e., Method 1B);

or (b) contacting the cyanomethylated monoethanolamine intermediate (II) with a hydroxide source (most preferably NaOH) and a metal-containing catalyst (most preferably a copper-containing catalyst) to concurrently hydrolyze and dehydrogenate the cyanomethylated monoethanolamine intermediate (II) (i.e., Method 2).

In an alternative process of the present invention, a monoethanolamine substrate is converted into an iminodiacetic acid compound in a process which comprises a dehydrogenation, followed by a cyanomethylation and a hydrolysis. Particularly preferred embodiments of this process are shown in Reaction Scheme 2.

Reaction Scheme 2

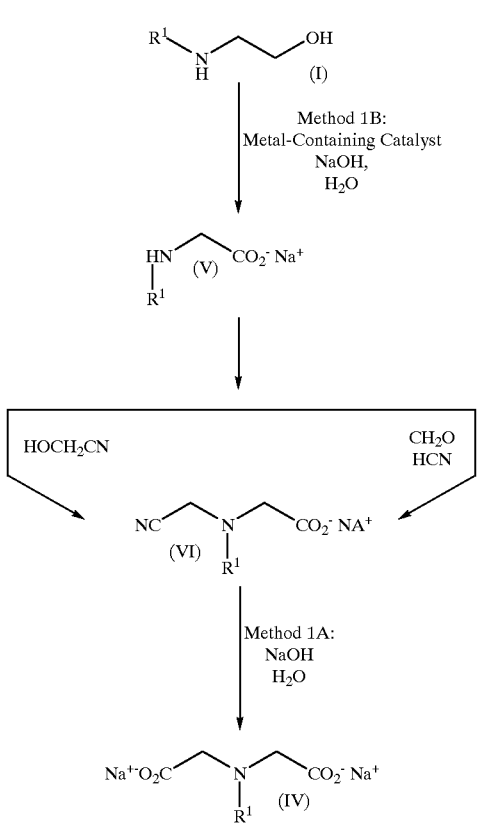

As shown in Reaction Scheme 2, a monoethanolamine substrate (1) is dehydrogenated to form a glycine intermediate (V) by contacting the monoethanolamine substrate (I) with a hydroxide source (most preferably NaOH) and a metal-containing catalyst (most preferably a copper-containing catalyst) (i.e., Method 1B). The glycine intermediate (V) is then cyanomethylated to form an N-cyanomethylated glycine intermediate (VI) by contacting the glycine intermediate (V) with either (a) glycolonitrile, or (b) $CH_2O$ and HCN. Finally, the N-cyanomethylated glycine intermediate (VI) is hydrolyzed to form the iminodiacetic acid product (IV) by contacting the N-cyanomethylated glycine intermediate (VI) with a hydroxide source (most preferably NaOH) (i e., Method 1A).

A. Cyanomethylation Reaction

The cyanomethylation reaction step of the present invention comprises contacting a monoethanolamine substrate (I) or a glycine intermediate (V) with a formaldehyde source and a cyanide source to produce, respectively, an N-cyanomethylated monoethanolamine intermediate (II) or an N-cyanomethylated glycine intermediate (VI). Typically, this reaction is conducted in an aqueous solution.

In general, the monoethanolamine substrate has the following structure (I):

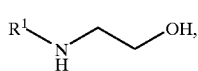 (I)

wherein $R^1$ is hydrogen, hydrocarbyl, or substituted hydrocarbyl. The glycine intermediate (V), on the other hand, has the following structure (V):

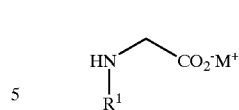 (V)

wherein $R^1$ is hydrogen, hydrocarbyl, or substituted hydrocarbyl; and $M^+$ is a hydrogen ion, alkali metal ion, alkaline earth metal ion, trialkylammonium ion, or tetraalkylammonium ion.

Formaldehyde sources useful in the process of the present invention may be present in a molecular form, in a partially or fully polymeric form, in an aqueous solution, or combined with cyanide in the form of glycolonitrile. Preferred forms of formaldehyde are formalin and aqueous glycolonitrile.

Cyanide sources useful in the process of the present invention include inorganic cyanides (e.g., HCN and alkali metal cyanides), or cyanide combined with formaldehyde in the form of glycolonitrile. Examples of suitable alkali metal cyanides are sodium cyanide, potassium cyanide, calcium cyanide and magnesium cyanide. Particularly preferred cyanide sources are HCN, aqueous glycolonitrile, and sodium cyanide.

The cyanide source and formaldehyde source preferably are present on a nearly equivalent basis to the monoethanolamine substrate (I) or glycine intermediate (V). Preferably, at least about 1.0 molar equivalent, more preferably from about 1.0 to about 2.0 molar equivalents, even more preferably from about 1.0 to about 1.2, and most preferably from about 1.0 to about 1.1 molar equivalents of cyanide source is introduced per mole of monoethanolamine substrate (I) or glycine intermediate (V) Preferably, at least about 1.0 molar equivalent, more preferably from about 1.0 to about 1.1 molar equivalent, and even more preferably from about 1.0 to about 1.05 molar equivalent of formaldehyde is introduced per mole of the monoethanolamine substrate (I) or glycine intermediate (V).

To minimize side reactions in the process, the formaldehyde source and the cyanide source are contacted with the monoethanolamine substrate (I) or the glycine intermediate (V) in a way that keeps the amount of unreacted formaldehyde as low as practical relative to the cyanide source and the unreacted monoethanolamine substrate (I) or unreacted glycine intermediate (V). Thus, it is generally preferred to add the formaldehyde source to the monoethanolamine substrate (I) or glycine intermediate (V) concurrently with or after the addition of the cyanide source. In one embodiment, the formaldehyde source and the cyanide source are introduced into a reaction vessel simultaneously with the monoethanolamine substrate (I) or glycine intermediate (V).

The reaction temperature for the cyanomethylation preferably is from about 0° to about 60° C., more preferably from about 5° to about 30° C., and still more preferably from about 5° to about 25° C. The preferred reaction time varies with the reaction temperature.

The cyanomethylation reaction may be carried out with or without pH control. It is preferable to avoid controlling the pH in a manner that generates a significant amount of salt residue and/or causes corrosion to the reactor system. Often, the reaction may be conducted without pH control. In such an instance, the pH of the cyanomethylation reaction will generally vary from about 9 to about 12. If desired, the pH can be controlled by adding a strong mineral acid (preferably HCl or $H_2SO_4$) or $CO_2$ before and/or as the reaction proceeds. When pH control is used, it is usually preferred to operate at a pH of from about 9 to about 10. As the cyanomethylation reaction proceeds, a strong alkali metal hydroxide may be added if the pH decreases below the preferred operating range. Preferred alkali metal hydroxides include lithium hydroxide, sodium hydroxide, potassium hydroxide, rubidium hydroxide, and cesium hydroxide, with sodium hydroxide and potassium hydroxide being particularly preferred.

The cyanomethylation reaction can be conducted in a batch mode or in a continuous mode. When the reaction is conducted in a continuous mode, the residence time in the reaction zone can vary widely, depending on the specific reactants and conditions employed. Typically, the preferred residence time is from about 15 minutes to about 10 hours, and more preferably from about 30 minutes to about 6 hours. When the reaction is conducted in a batch mode, the preferred reaction time is typically from about 1 to about 10 hours, and more preferably from about 2 to about 6 hours.

B. Hydrolysis Reaction-Method 1A

The hydrolysis step of this invention comprises contacting an N-cyanomethylated monoethanolamine intermediate (II) or an N-cyanomethylated glycine intermediate (VI) with a hydroxide source (particularly water) to form, respectively, an N-(2-hydroxyethyl)glycine intermediate (III) or an iminodiacetic acid product (IV).

Preferably the hydroxide source comprises a strong base. Suitable bases include, for example, an alkali metal hydroxide, a tetraalkyl ammonium hydroxide having up to 5 carbon atoms in each alkyl group (e.g., tetramethyl ammonium hydroxide, dimethyldipropyl ammonium hydroxide, tributylethyl ammonium hydroxide, and the like), or other strong organic bases (e.g., guanidine and aminoguanidine). Alkali metal hydroxides are particularly preferred, and include lithium hydroxide, sodium hydroxide, potassium hydroxide, rubidium hydroxide, and cesium hydroxide. Because of their ready availability and ease of handling, sodium hydroxide and potassium hydroxide are generally the more preferred, with sodium hydroxide being most preferred. The preferred amount of hydroxide base is typically from about 1 to about 4 molar equivalents of base relative to the cyano group of the N-cyanomethylated monoethanolamine intermediate (II) or the cyanomethylated glycine intermediate (VI). Use of at least about 1 molar equivalent is preferred. The hydroxide source is typically introduced into the reaction zone in the form of flakes, powder, pellets, or an aqueous solution.

The preferred reaction temperature for the hydrolysis is typically from about 0° to about 100° C., and more preferably from about 20° to about 60° C. The preferred reaction time varies with the reaction temperature.

The hydrolysis may be conducted over a wide pressure range at the temperatures indicated above. Generally, the minimum pressure is selected to be greater than the lowest pressure at which the reaction proceeds in the liquid phase.

The hydrolysis reaction is typically conducted at a pressure of from about 5 to about 420 psia (i.e., from about 35 to about 2940 kPa), more preferably from about 28 to about 350 psia (i.e., from about 196 to about 2550 kPa), and still more preferably from about 70 to about 280 psia (i.e., from about 490 to about 1960 kPa).

The hydrolysis reaction may be conducted in a batch mode or a continuous mode. When the hydrolysis is conducted in a continuous mode, the residence time can vary widely, depending on the specific reactants and conditions employed. Typically, residence time is from about 15 minutes to about 20 hours, and more preferably from about 4 to about 12 hours. When the hydrolysis is conducted in a batch mode, the reaction time typically is from about 1 to about 10 hours, and more preferably from about 2 to about 6 hours.

C. Dehydrogenation Reaction-Method 1B

1. Reaction Conditions

The dehydrogenation step of this invention comprises contacting an N-(2-hydroxyethyl)glycine intermediate (III) or a monoethanolamine substrate (1) with a metal-containing catalyst to form, respectively, an iminodiacetic acid product (IV) or a glycine intermediate (V).

Normally, this reaction is conducted in the presence of a hydroxide source. The hydroxide source is typically a strong base having a $pK_a$ value of at least about 11, more preferably at least about 12, and even more preferably at least about 13. Suitable bases include, for example, alkali metal hydroxides (e.g., LiOH, NaOH, KOH, RbOH, or CsOH), alkaline-earth metal hydroxides (e.g., $Mg(OH)_2$ or $Ca(OH)_2$), NaH, and tetramethyl ammonium hydroxide. Of these bases, alkali metal hydroxides (particularly NaOH and KOH) are often preferred because of their solubility in water under the reaction conditions, as well as their ready commercial availability and ease of handling.

Preferably, at least about 1.0 molar equivalent (more preferably from about 1.0 to about 3.0 molar equivalents, even more preferably from about 1.05 to about 2.0 molar equivalents) of base is introduced per mole of the alcohol reactant. The hydroxide may, for example, be in the form of flakes, powder, pellets, or an aqueous solution.

The reaction is normally conducted in a solvent in which the base is soluble. Preferably, a sufficient quantity of solvent is present in the reaction zone to dissolve essentially all (more preferably, all) the base. The solvent also preferably is present in a sufficient quantity to maintain the alcohol reactant and carboxylic acid salt product in a solubilized form. Water is normally the preferred solvent due to its low cost, widespread availability, and ease of handling.

The preferred catalyst loading (i.e., the preferred amount of catalyst introduced into the reaction zone) depends on, for example, the amount of the alcohol reactant introduced into the reaction zone. Typically, the catalyst loading is at least about 1% by weight of the alcohol reactant (i.e., [mass of catalyst÷mass of alcohol reactant]×100%). More preferably, the catalyst loading is from about 1 to about 70% (still more preferably from about 1 to about 40%, and still yet more preferably from about 10 to about 40%) by weight of the alcohol reactant.

The preferred catalyst loading also depends on, for example, the amount of total reaction mass. Typically, the catalyst loading is at least about 0.1% by weight of the total reaction mass (i.e., [mass of catalyst÷total reaction mass]× 100%). More preferably, the catalyst loading is from about 0.1 to about 10% (even more preferably from about 3.5 to about 10%, and still even more preferably from about 3.5 to about 5%) by weight of the total reaction mass. Concentrations of greater than about 10 wt. % are difficult to filter. On the other hand, concentrations of less than about 0.1 wt. % tend to produce unacceptably low reaction rates.

The reaction typically is conducted at a temperature of at least about 70° C., preferably from about 120° to about 220° C., more preferably from about 140° to about 200° C. and even more preferably from about 145° to about 165° C. Although a reaction temperature outside of these ranges may be used, the results are typically less than optimal.

The reaction is preferably conducted under pressure. More particularly, the reaction is normally conducted under a pressure which is sufficient to prevent boiling of the mixture at the reaction temperature. At reaction temperatures of from about 120° to about 220° C., the pressure preferably is at least about 28 psia (i.e., at least about 196 kPa), more preferably from about 28 to about 420 psia (i.e., from about 196 to about 2940 kPa), and still more preferably from about 70 to about 280 psia (i.e., from about 490 to about 1960 kPa). Although greater pressures may be used, they are normally less desirable because they tend to reduce the reaction rate.

The dehydrogenation may be conducted in the absence of a purge gas. Alternatively, the dehydrogenation may be conducted in the presence of an oxygen atmosphere to convert the evolved $H_2$ into water, as described by Ochoa Gomez et al. in U.S. Pat. No. 5,225,592. In yet another embodiment, the dehydrogenation reaction is conducted under a non-oxidizing atmosphere (preferably, an atmosphere containing a noble gas (e.g., Ar), $H_2$, and/or $N_2$, and more preferably $N_2$ when the reaction is conducted on a commercial level) to avoid oxidation of the catalyst surface (the atmosphere will also contain $H_2$ which evolves during the dehydrogenation).

The dehydrogenation reaction may be carried out in a wide variety of batch, semi-batch, and continuous reactor systems. Suitable conventional reactor configurations include, for example, stirred-tank reactors, fixed bed reactors, trickle bed reactors, fluidized bed reactors, bubble flow reactors, plug flow reactors, and parallel flow reactors. Often, the more preferred reactor configurations are stirred-tank reactors.

When the dehydrogenation is conducted in a continuous reactor system, the residence time in the reaction zone can vary widely depending on the specific catalyst and conditions employed. Likewise, when the dehydrogenation is conducted in a batch reactor, the reaction time typically will also vary widely depending on such factors. Normally, the dehydrogenation behaves as a first order reaction, particularly toward the end of the reaction. Thus, the preferred residence time in a continuous reaction zone (or the preferred reaction time in a batch reaction zone) will also depend on the desired degree of conversion. Typically, when the dehydrogenation is conducted in a continuous reaction zone, the preferred residence time is from about 15 minutes to about 20 hours, and more preferably from about 4 to about 12 hours. When the dehydrogenation is conducted in a batch reaction zone, the preferred reaction time is typically from about 1 to about 10 hours, and more preferably from about 2 to about 6 hours.

2. Dehydrogenation Catalyst

Suitable catalysts for the dehydrogenation reaction include those known in the art for dehydrogenating ethanolamines to corresponding amino acid salts. Such catalysts include, for example, metallic forms of cadmium, copper, nickel, silver, lead, and zinc, as well as various compounds of these metals. Chitwood (U.S. Pat. No. 2,384,817), for example, reports that cadmium oxide, cadmium acetate, mossy cadmium metal, cupric oxide, powdered copper metal, nickelous oxide, nickel sponge, silver oxide, powdered silver metal, lead acetate, lead dioxide, and zinc oxide metallic catalysts are suitable for catalyzing the dehydrogenation of primary alcohols. Copper sponge has also been reported to be an effective catalyst. See, e.g., Goto et al., U.S. Pat. No. 4,782,183; PCT Pub. No. WO2906069; and Franczyk et al., U.S. Pat. Nos. 5,739,390; 5,367,112; and 5,292,936.

In a particularly preferred embodiment, the catalyst comprises a metal (e.g., copper, cobalt, nickel, cadmium, or mixtures thereof) deposited on a relatively hydroxide resistant support along with an anchor metal. A detailed discussion of such catalysts may be found in Ebner et al.'s U.S. Pat. No. 5,627,125. Of these catalysts, the more preferred are those which comprise catalytically active copper anchored with platinum, palladium, ruthenium, gold or mixtures thereof on a titanium oxide, zirconium oxide, or carbon (particularly activated carbon) support. For convenience, such catalysts are sometimes referred to herein as "anchored-metal catalysts."

In another particularly preferred embodiment, the catalyst comprises copper and at least one other metal which, at least in part, provides strengthening characteristics to the copper to make a more durable catalyst. Such a catalyst is advantageous because the softness of copper is at least one of the reasons that many traditional copper-containing catalysts (particularly copper sponge catalysts, such as those described by Goto et al. in U.S. Pat. No. 4,782,183) deactivate over time. More specifically, as such catalysts are used, their surfaces tend to lose surface area and the catalyst particles themselves tend to agglomerate (this agglomeration, in turn, reduces access by the reactants to the catalyst's active sites). These effects are particularly pronounced when the traditional catalysts are used in a stirred-tank reactor (or otherwise subjected to mechanical agitation). Both the loss of surface area and the agglomeration of the catalyst particles reduce the surface area of the catalyst, thereby reducing activity of the catalyst.

a. Catalysts Comprising Copper on a Metal Support

In one embodiment of this invention, the dehydrogenation catalyst comprises a copper-containing active phase at the surface of an internal supporting structure. Preferably, the supporting structure is resistant to deformation under the conditions of the dehydrogenation reaction. The catalyst may comprise a homogeneous structure such as a monophasic alloy or a heterogenous structure having more than one discrete phase. Thus, the copper-containing active phase may be present at the surface of the supporting structure as a discrete phase such as a copper coating or an outer stratum, as a surface stratum, or as part of a homogeneous structure. It is important to note that in the case of a copper-containing active phase comprising an outer stratum of the catalyst, the internal supporting structure may be totally or partially covered by the copper-containing active phase.

Typically, the copper-containing active phase has a copper concentration of at least about 50% by weight copper, more preferably at least about 75% by weight copper, even more preferably at least about 90% by weight copper, and most preferably at least about 95% by weight copper. When the copper-containing active phase is present as a surface stratum, outer stratum or as a discrete phase or coating, the surface of the support preferably comprises from about 0.005 to about 0.5 grams (more preferably from about 0.03 to about 0.5 grams, even more preferably from about 0.08 to about 0.35 grams) of copper per gram of said metal support. In other words, the catalyst preferably contains copper deposited at the surface of the metal support in a concentration ranging from about 0.005 to about 0.5 grams (more preferably from about 0.03 to about 0.5 grams, even more preferably from about 0.08 to about 0.35 grams) of copper for every gram of metal support.

i. Supporting Structure

The supporting structure may comprise any material suitable for supporting a copper-containing active phase, preferably any non-brittle material having a tensile strength and/or yield strength greater than copper. The supporting structure typically comprises a metal support. Suitable metal supports may comprise a wide variety of compositions. In general, however, at least about 10% by weight of the metal support is non-copper metal. In one particularly preferred embodiment, at least about 50% (more preferably at least about 65%, about 80%, about 85% or even at least about 90%/o) by weight of the metal support is non-copper metal (this non-copper metal may comprise a single metal or multiple metals). In another particularly preferred embodiment, at least about 50% (more preferably from about 60% to about 80%) by weight of the metal support is copper.

The metal or alloy from which the metal support is made preferably has a tensile strength and/or yield strength which is greater than copper alone. It is particularly preferred for the catalyst composition to have a yield strength of greater than about 70 Mpa, more preferably greater than 100 Mpa, and even more preferably at least 110 Mpa. It is also particularly preferred for the catalyst composition to have a tensile strength of greater than 221 Mpa, more preferably greater than 275 Mpa, and even more preferably greater than 300 Mpa. For example, a composition containing 70% by weight copper and 30% by weight zinc reportedly has a yield strength of 124 Mpa and a tensile strength of 331 Mpa; a composition containing 90% by weight copper and 10% by weight nickel reportedly has a yield strength of 110 Mpa and a tensile strength of 303 Mpa; and a composition containing 70% by weight copper and 30% by weight nickel reportedly has a yield strength of 138 Mpa and a tensile strength of 372 Mpa. See A. S. Krisher and O. W. Siebert in *Perry's Chemical Engineers' Handbook*, pp. 23–42 to 23–49 (6th ed., R. H. Perry, D. Green, and J. O. Maloney, eds, McGraw Hill, New York, N.Y. 1984).

In many instances, it is preferred for the non-copper metal in the support to be relatively non-reactive in the alkaline (and often chelating) environments of the dehydrogenation reaction. Such metals include, for example, nickel, gold, palladium, and platinum. Of these metals, nickel is typically the more preferred because, for example: (1) nickel generally costs less than the other metals, and (2) depositing copper onto a nickel-containing support is typically less difficult relative to depositing copper onto a support containing a significant amount of the other listed metals. For example, copper may be deposited onto a nickel-containing support using the simple process of electrochemical displacement deposition. There are, however, other techniques (e.g., electroless plating and metal-organic chemical vapor deposition) which may often be used to deposit copper onto supports comprising gold, palladium, and/or platinum.

It should be recognized that, other metals (e.g., zinc, cobalt, iron, and tin) which show some reactivity in alkaline and/or chelating environments also may often be suitable. This is particularly true because the copper at the surface of the metal support tends to act as a shield to protect the metal in the support from the reaction environment. Also, a less-alkaline-resistant metal may provide other advantages over a more-alkaline-resistant metal. For example, it is often desirable to deposit copper onto the surface of the metal support using electrochemical displacement deposition (also described in the art as "immersion plating"). In that instance, the metal support preferably contains metal having a reduction potential to the metal which is less than the reduction potential to the metal of copper, i.e., a reduction potential to the metal of less than about +343 mVolts vs. NHE (normal hydrogen electrode). Metals having such a reduction potential include, for example, nickel, zinc, tin, iron, and cobalt. The presence of such a metal near the surface of the support allows for simple deposition of copper metal at the surface of the support by contacting the surface with a copper salt solution. Typically such a copper salt solution comprises a copper salt having copper present in the divalent state (e.g., a Cu(II) salt solution). More specifically, during displacement deposition, such a metal near the surface of the support tends to oxidize (and go into solution as an ion) when contacted with a copper ion solution. As this occurs, the copper ions in solution near the support surface are reduced to copper metal, which, in turn, deposits on the surface of the support. The reaction which occurs, for example, when a support comprising nickel is contacted with a copper salt solution is:

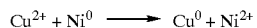

$$Cu^{2+} + Ni^0 \longrightarrow Cu^0 + Ni^{2+}$$

As the foregoing suggests, when the catalyst is prepared by depositing copper onto the surface of the support using displacement deposition, a nickel-containing support is particularly preferred because nickel has a reduction potential to the metal which is less than the reduction potential to the metal of copper, nickel is relatively stable in the reaction conditions of the dehydrogenation reaction, and nickel has a greater mechanical strength and resistance to attrition than copper.

When the metal support comprises more than one metal, it is preferred that at least about 80% by weight (more preferably at least about 85% by weight, even more preferably at least about 90% by weight, and still even more preferably essentially all) of the metals in the support are in the form of an alloy. In a particularly preferred embodiment, the metals form a substitutional alloy (also known as a "monophasic alloy"), wherein the alloy has a single, continuous phase. Although multiphasic alloys (i.e., alloys comprising at least 2 discrete phases) may be used, monophasic alloys are generally preferred because it is difficult to evenly distribute copper onto a multiphasic support surface because copper tends to preferentially coat the copper-rich portions relative to the copper-poor portions of the surface. Whether the alloy is monophasic or multiphasic will depend on the components of the alloy and their concentrations. Typically, for example, metal supports consisting essentially of nickel and copper are monophasic at any nickel concentration. But when, for example, the support consists essentially of copper and zinc, there are many zinc concentrations (typically, concentrations greater than about 35% by weight) which lead to the alloy being bi-phasic.

It should be recognized that the support may also comprise non-metal atoms (e.g., boron, carbon, silicon, nitrogen, phosphorus, etc.) in addition to the metal atoms. An alloy containing such non-metal is typically described in the art as an "interstitial alloy." Supports comprising such an alloy may have various advantages, such as enhanced mechanical strength. Typically, however, catalysts comprising an interstitial alloy contain at least about 70% metal.

In a particularly preferred embodiment, the metal support is a metal sponge. As used herein, the term "metal sponge" refers to a finely divided and porous form of metal having a surface area of at least about 20 m$^2$/g, and more typically at least about 35 m$^2$/g. Such surface area may be measured using, for example, the B.E.T. (Brunauer/Emmett/Teller) method which is well known in the art. It has been found in accordance with this invention that if copper is deposited at the surface of a metal sponge support, the resulting material exhibits the mechanical strength and high surface area of the sponge support combined with the desired catalytic activity of the copper.

Metal sponges are available from W. R. Grace & Co. under the trademark "Raney" and are often generally described in the art as "Raney metals," irrespective of source. Applicants use the term "metal sponge" rather than "Raney metal" to ensure that the claims appended hereto are not limited to the use of W. R. Grace & Co.'s metal sponges.

Typically, the preferred average particle size of the metal sponge is at least about 0.1 μm, preferably from about 0.5 to about 100 μm, more preferably from about 15 to about 100 μm, even more preferably from about 15 to about 75 μm, and still even more preferably from about 20 to about 65 μm.

Sponge supports can be prepared by techniques generally known to those skilled in the art. See, generally, E. Lieber and F. L. Morritz, *Adv. Catal.*, 5, 417 (1953) (a general review directed to sponge metals). In general, techniques for making metal sponges comprise forming an alloy which contains about 50% by weight of a leachable metal (typically aluminum) and about 50% by weight of the desired metal(s); grinding the alloy to a desired particle size; and treating the alloy particles with an aqueous solution of an alkali metal hydroxide (preferably NaOH) to leach at least a portion of the leachable metal from the alloy. It is often preferred to conduct the leaching at a temperature of less than about 50° C. (more preferably no greater than about 40° C., and even more preferably from about 20° to about 40° C.). As the leachable metal leaches from the particle, it leaves behind voids (e.g., pores) which dramatically increase the surface area of the particle.

It should be recognized that the above-described technique is not the only method for making sponge metals. An iron sponge, for example, may be formed by reducing iron oxide at such low temperatures that melting does not occur, typically by mixing iron oxide and coke and applying a limited increase in temperature. See Hawley's *Condensed Chemical Dictionary* 13th Ed., p. 621 (Rev. by Richard J. Lewis, Sr., Van Nostrand Reinhold, New York, N.Y. 1997).

References describing the preparation of nickel sponges include, for example, Augustine, Robert L., *Catalytic Hydrogenation Techniques and Applications in Organic Synthesis* (Marcel Dekker, Inc., 1965), appendix at pp. 147–149. See also, *Hawley's Condensed Chemical Dictionary*, 13th Ed., p. 955 (Rev. by Richard J. Lewis, Sr., Van Nostrand Reinhold, New York, N.Y. 1997) (describing the generally recognized technique of making sponge nickel by leaching aluminum from an alloy containing 50% by weight nickel and 50% by weight aluminum using a 25% by weight caustic soda solution).

References describing the preparation of nickel/copper sponges include, for example, D. J. Young, M. S. Wainwright, and R. B. Anderson, *J. Catal.*, 64, 116 (1980). Such references also include, for example, M. S. Wainwright and R. B. Anderson, *J. Catal.*, 64, 124 (1980).

References describing the preparation of copper/zinc sponges include, for example, A. J. Bridgewater, M. S. Wainwright, D. J. Young, and J. P. Orchard, *Appl. Catal.*, 7, 369 (1983). Such references also include, for example, M. S. Wainwright, "Raney Copper and Raney Copper-Zinc Catalysts," *Chem. Ind.* (Dekker), 68, 213–30 (1996).

References describing the preparation of nickel/iron sponges include, for example, H. J. Becker and W. Schmidt in "Raney nickel-iron catalyst," *Ger. Offen.* DE 2713374 19780928 (1978).

References describing the preparation of nickel/cobalt sponges include, for example, J. P. Orchard, A. D. Tomsett, M. S. Wainwright, and D. J. Young in "Preparation and Properties of Raney Nickel-Cobalt Catalysts," *J. Catal.*, vol. 84, pp. 189–99 (1983).

Various metal sponges are also commercially available from, for example, W. R. Grace & Co. (Chattanooga, Tenn.); Gorwara Chemical Industries (Udaipur, India); Activated Metals & Chemicals, Inc. (Sevierville, Tenn.); Degussa-Huls Corp. (Ridgefield Park, N.J.); Engelhard Corp. (Iselin, N.J.); and Aldrich Chemical Co. (Milwaukee, Wis.).

Examples of suitable commercially-available nickel sponges, for example, include Raney® 2800 (characterized by the manufacturer as having at least 89 wt. % Ni; no greater than 9.5 wt. % Al; no greater than 0.8 wt. % Fe; an average particle size in the range of 20–60 μm; a specific gravity of approximately 7; and a bulk density of 15–17 lbs/gal based on a catalyst slurry weight of 56% solids in water), Raney® 4200 (characterized by the manufacturer as having at least 93 wt. % Ni; no greater than 6.5 wt. % Al; no greater than 0.8 wt. % Fe; an average particle size in the range of 20–50 μm; a specific gravity of approximately 7; and a bulk density of 15–17 lbs/gal based on a catalyst slurry weight of 56% solids in water), Raney® 4310 (characterized by the manufacturer as having at least 90 wt. % Ni; no greater than 8 wt. % Al; 0.5–2.5 wt. % Mo; no greater than 0.8 wt. % Fe; an average particle size in the range of 20–50 μm; a specific gravity of approximately 7; and a bulk density of 15–17 lbs/gal based on a catalyst slurry weight of 56% solids in water), Raney® 3110 (characterized by the manufacturer as having at least 90 wt. % Ni; 0.5–1.5 wt. % Mo; no greater than 8.0 wt. % Al; no greater than 0.8 wt. % Fe; an average particle size in the range of 25–65 μm; a specific gravity of approximately 7; and a bulk density of 15–17 lbs/gal based on a catalyst slurry weight of 56% solids in water), Raney® 3201 (characterized by the manufacturer as having at least 92 wt. % Ni; no greater than 6 wt. % Al; no greater than 0.8 wt. % Fe; 0.5–1.5 wt. % Mo; an average particle size in the range of 20–55 μm; a specific gravity of approximately 7; and a bulk density of 15–17 lbs/gal based on a catalyst slurry weight of 56% solids in water), Raneyt 3300 (characterized in U.S. Pat. No. 5,922,921 as having 90–99.1 wt. % Ni; no greater than 8.0 wt. % Al; no greater than 0.8 wt. % Fe; 0.5–1.5 wt. % Mo; no greater than 0.8 wt. % Ni; an average particle size in the range of 25–65 μm; a specific gravity of approximately 7; and a bulk density of 15–17 lbs/gal based on a catalyst slurry weight of 56% solids in water), Raney® 2724 (Cr-promoted), and Raneyg 2724 (Cr-promoted), all sold by W. R. Grace & Co.; the catalyst described as "Raney nickel" sold by Gorwara Chemical Industries; A-4000 and A-5000, sold by Activated Metals & Chemicals, Inc.; nickel ABMC, sold by Degussa-Huls Corp.; and "Raney nickel," Catalog No. 22,167–8, sold by Aldrich Chemical Co.

Examples of suitable commercially-available cobalt sponges include Raney® 2700 (characterized in U.S. Pat. No. 5,922,921 as having 93.0 wt. % Co; no greater than 6.0 wt. % Al; no greater than 0.7 wt. % Fe; no greater than 0.8 wt. % Ni; an average particle size in the range of 20–50 μm; a specific gravity of approximately 7; and a bulk density of 15–17 lbs/gal based on a catalyst slurry weight of 56% solids in water), sold by W. R. Grace & Co.; the cobalt sponge catalysts reportedly manufactured by the Raney process and sold by Activated Metals & Chemicals, Inc.; and cobalt ABMC, sold by Degussa-Huls Corp.

b. Deposition of the Copper-containing Active Phase

The copper-containing active phase may be deposited at the surface of a metal support using various techniques well-known in the art for depositing metal onto metal surfaces. These techniques include, for example, liquid phase methods, such as electrochemical displacement deposition and electroless plating; and vapor phase methods such as physical deposition and chemical deposition. The following discussion will focus on the two particularly preferred techniques of electrochemical displacement deposition and electroless plating. This preference stems from the fact that the other techniques are generally more complicated and/or more costly.

It is important to note that copper is at least partially miscible with most support metals of interest and is completely miscible with nickel. Thus, it has been found that the copper deposition process may result in the catalyst having copper, or more particularly a copper-containing active phase, at the surface as part of a discrete phase such as an outer stratum or coating; at the surface as part of a surface stratum; or the copper may migrate from the surface of the support into the bulk of the support. Without being held to a particular theory, it is believed that the catalyst surface can move, sinter or otherwise restructure during the reaction conditions of the deposition process resulting in such variations of form in the copper-containing active phase. Nonetheless, it has been found that the copper deposition process results in an overall increase in the copper content of the catalyst with the deposited copper predominantly present at or near the surface of the catalyst, which is richer in copper than before deposition.

i. Electrochemical Displacement Deposition of Copper

Copper may be deposited onto the surface of the supporting structure via electrochemical displacement deposition wherein copper ions in a copper-salt solution in contact with the support are reduced to copper metal as non-copper metal near the surface of the support is oxidized. The copper metal, in turn, forms a coating on the surface of the support, while the non-copper ions go into solution. A general discussion related to electrochemical displacement deposition may be found in, for example, G. A. Krulik and N. V. Mandich, "Metallic Coatings (Survey)", *Kirk-Othmer Encyclopedia of Chemical Technology* 4th Ed. (J. I. Kroschwitz and M. Howe-Grant, eds., Wiley, New York, N.Y., 1995) Vol. 16, pp. 258–91.

Without providing an exhaustive list, suitable copper salts for displacement deposition include, for example, the nitrate, sulfate, chloride, and acetate salts of copper. Salts containing copper in the divalent state (i.e., Cu(II)) are typically the most preferred. Although salts containing monovalent and trivalent copper may be used, they are typically less preferred because they tend to be unstable, commercially less available, and/or insoluble in the alkaline mixture.

Before and during the displacement deposition, the metal support preferably is protected from air by, for example, keeping it immersed in water, maintaining it under a non-oxidizing atmosphere (noble gas or $N_2$, preferably $N_2$), and/or sparging a suspension containing the support with a non-oxidizing gas. In one particularly preferred embodiment, the metal support surface is reduced before the displacement deposition. The surface may be reduced, for example, by contacting the support with a solution of sodium borohydride ($NaBH_4$), formaldehyde, or other reducing agent; or by contacting the support with $H_2$ or another reducing gas at an elevated temperature. Example 5 demonstrates such a technique.

To initiate the displacement deposition, the copper salt may be added as a dry powder to a solution containing the metal support, but more preferably is added as an aqueous solution. While adding the copper salt, the solution containing the metal support preferably is gently stirred at a rate sufficient to keep the support particles suspended. Although the copper salt may be added all at once, the salt is preferably added slowly so that the salt concentration does not exceed the concentration at which the salt begins to precipitate. Typically, the salt is added over a period of at least about 30 minutes, but no greater than about 2 hours (such slow salt addition is often unnecessary in the presence of a strong chelating agent, such as ethylenediaminetetraacetic acid, which keeps the copper salt solubilized). After the salt has been added, the resulting mixture preferably is stirred for at least about 15 minutes. Afterward, the stirring may be discontinued so that the catalyst can settle to allow the supernatant to be removed by decantation or other means.

The catalyst may then be re-suspended in the desired solvent for introduction into the dehydrogenation reaction zone.

During the displacement deposition, the pH of the solution containing the metal support preferably is adjusted so that the displaced metal will tend to remain soluble and not redeposit onto the support. Metal ions are generally more soluble under acidic conditions than basic conditions (with the exception of alkali metal ions, which are generally soluble under both acidic and basic conditions). Thus, the pH is preferably low enough to ensure that the displaced metal remains in solution and does not redeposit onto the catalyst as, for example, an oxide or hydroxide.

If, during the displacement deposition, the copper is deposited at a rate which tends to unevenly coat the support, a more even coating may often be obtained by including a protecting chelating agent in the copper salt solution to control (i.e., slow) the rate of copper deposition so that a more even coat may be obtained. A chelating agent may also be beneficial to inhibit the displaced metal from redepositing onto the metal support. Suitable chelating agents include, for example, hydroxy carboxylic acids (e.g., lactic acid, malic acid, citric acid, and tartaric acid) and salts thereof (e.g., sodium potassium tartrate, also described in the art as "Rochelle salt"), with tartaric acid and salts thereof being preferred. Chelators which contain amines (e.g., salts of iminodiacetic acid, nitrilotriacetic acid, and particularly ethylenediaminetetraacetic acid (also known as "EDTA")) are particularly preferred, for example, for depositing copper on metal supports comprising nickel. Normally, at least one molar equivalent (based on moles of copper ions) of chelating agent is preferably included. Even more preferably, from about 1.2 to about 3.0 (still even more preferably from about 1.2 to about 1.8) molar equivalents of chelating agent are included in the mixture. Although concentrations of greater than 3.0 molar equivalents may be used, such additional concentrations usually do not provide any greater benefits. Concentrations of greater than 3.0 molar equivalents also tend to cause the chelating agent to precipitate and may create greater burdens downstream during product purification.

Examples 13–16 and 21 illustrate electrochemical displacement deposition of copper onto a metal sponge support. The same examples also illustrate the use of a chelating agent during such a deposition.

In a particularly preferred method for the deposition of copper onto a metal support, electrochemical displacement deposition is conducted under basic conditions followed by electrochemical displacement deposition under acidic conditions. Preferably, the metal support is free of surface oxidation at the time of the plating. However, in instances where the metal support has an oxidized surface (i.e., when the support has been exposed to air (even while under water) for 6 or more months), it is particularly preferable to pre-treat the support with a reducing agent. For example, the support may be stirred in a sodium borohydride solution, which preferably comprises a solution having a pH of at least about 10 and at least about 1 gram of sodium borohydride per 25 grams of metal support. Generally, contacting the support with the reducing agent for about 5 minutes to about 2 hours at room temperature is sufficient.

To begin the electrochemical displacement deposition, the catalyst support is slurried into a water or alcohol solution, preferably in water, and the pH is adjusted to 7. A copper salt as described above is added to the metal support slurry, preferably as a solution comprising the copper salt and a chelator, particularly an amine chelator such as EDTA. Preferably, the copper salt solution contains about 10% to about 30% copper by weight with respect to the metal support. A solution of an alkali metal hydroxide (such as NaOH) or another suitable base is then slowly added to the slurry, preferably with continuous stirring and nitrogen sparging. The alkali metal hydroxide solution preferably contains at least one equivalent of alkali metal hydroxide with respect to the copper salt, and more preferably three equivalents of alkali metal hydroxide with respect to the copper salt. Although this step comprises a displacement deposition reaction, a majority of the oxidized metal from the support remains closely associated with the support and is removed in the subsequent acidic step. Moreover, the first, basic displacement deposition reaction results in the deposition of cuprous oxide as well as metallic copper at the surface of the support.

After the basic displacement deposition, the supernatant is removed by decanting or other means and copper is further deposited onto the surface of the catalyst support under acidic conditions. After decantation, the metal support is again slurried into an alcohol or water solution. An acid buffer solution, preferably a gluconic acid/gluconate buffer, is added to the metal support slurry to reduce the pH to below about 4. The temperature of the buffer is preferably between about 40° and about 90° C. The acid buffer may comprise any suitable chelator which is capable of controlling residual metals in solution while subsequently lowering pH. For example, gluconic acid is preferred for depositing copper onto the surface of metal supports comprising nickel because gluconic acid is a good chelator for residual aluminum ions present in solution. A copper salt as described above is then added to the metal support slurry, preferably as a copper salt solution, over a period of about 5 to about 40 minutes with continuous stirring and nitrogen sparging. Afterward, the stirring may be discontinued so that the catalyst can settle to allow the supernatant to be removed by decantation or other means. The catalyst may then be re-suspended in the desired solvent for introduction into the dehydrogenation reaction zone.

ii. Electroless Plating of Copper

Electroless plating may alternatively be used to deposit copper onto the surface of the support. Like displacement deposition, electroless plating comprises reducing copper ions to copper metal in a solution in contact with the support. However, unlike displacement deposition, substantially all the copper ions are reduced by an external reducing agent rather than the support itself. As the reducing agent reduces the copper ions in the solution to copper metal, the copper metal forms a coating on the surface of the support. It is generally preferred for electrochemical displacement plating to be suppressed during electroless plating. This is preferably accomplished by the presence of chelators, such as the amine chelators discussed above (particularly salts of EDTA). The chelator is preferably added to the copper ion solution before contacting the metal support to avoid electrochemical displacement deposition from occurring in the absence of the reducing agent.

Suitable sources of copper ion for use in electroless plating include copper salts including, for example, the nitrate, sulfate, chloride, acetate, oxalate, and formate salts of copper. Salts containing copper in the divalent state (i.e., Cu(II)) are typically the most preferred. Although salts containing monovalent and trivalent copper may be used, they are typically less preferred because they tend to be unstable, commercially less available, and/or insoluble in the alkaline mixture. Other sources may include copper complexes such as copper decanoates, copper naphthanates and copper acetylacetonate.

The copper ion solution may be aqueous or non-aqueous. Suitable non-aqueous solvents generally include alcohols, liquid aromatic hydrocarbons such as benzene and toluene, mineral spirits and THF.

A wide variety of suitable reducing agents may be used. These include, for example, sodium hypophosphite ($NaH_2PO_2$), formaldehyde ($CH_2O$) and other aldehydes, formic acid (HCOOH), salts of formic acid, salts of borohydride (e.g., sodium borohydride ($NaBH_4$), salts of substituted borohydrides (e.g., sodium triacetoxyborohydride ($Na(CH_3CO_2)_3BH$), sodium alkoxides, and hydrazine ($H_2NNH_2$). Sodium borohydride is a particularly preferred reducing agent in aqueous electroless plating methods because it is readily available, may be solubilized without heating, and has sufficient activity at room temperature to enable plating to be completed within about 1 hour. For platings in non-aqueous copper ion solutions, the preferred reducing agent is gaseous hydrogen owing to the good solubility of hydrogen in organic solvents.

In an aqueous electroless plating method, the reducing agent is typically added slowly (preferably over a period of from about 5 minutes to 3 hours, and more preferably from about 15 minutes to about 1 hour) to a slurry of the metal support in water or an alcohol under an inert atmosphere (e.g., $N_2$). If the reducing agent is instead first added to the copper salt, it is preferably added to a solution which contains the copper salt and also a chelator (the presence of the chelator inhibits the reduction of the copper ions before the copper-salt solution is contacted with the metal support).

The metal support preferably is essentially free of surface oxidation at the time of the plating. Consequently, in instances where the metal support has an oxidized surface (such as when the support has been exposed to air (even while under water) for 6 or more months), it is particularly preferable to pre-treat the support with a reducing agent. For example, the support may be stirred in a sodium borohydride solution, which preferably comprises a solution having a pH of at least about 10 and at least about 1 gram of sodium borohydride per 25 grams of metal support. Contacting the support with the reducing agent for about 5 minutes to about 2 hours at room temperature is generally sufficient to remove surface oxidation.

Examples 17–19 and 23 illustrate the use of electroless plating to deposit copper onto the surface of a metal support.

c. Other Copper-containing Catalysts

In another embodiment of this invention, the dehydrogenation catalyst does not comprise a copper-containing active phase deposited at the surface of a metal support (i.e., there is no discrete copper deposited on or coating the surface of the catalyst). Rather, the copper is mixed (preferably in the form of an alloy) with other metals which provide desirable properties to provide a catalyst active phase. In this embodiment, from about 10% to about 85% (more preferably from about 50% to about 85%, even more preferably from about 60% to about 80%, and still more preferably from about 60% to about 75%) by weight of the catalyst is copper. Preferably, the catalyst is in the form of a metal sponge. In a particularly preferred embodiment, the catalyst comprises greater than about 1% by weight nickel, tin, or a combination thereof. In another particularly preferred embodiment, the catalyst comprises less than about 1% by weight metal oxide.

It should be recognized that this embodiment is less preferred if there are significant adverse effects from the non-copper metal of the catalyst being in contact with the other components in the reaction zone. For example, a catalyst having a copper coating is more preferred if the catalyst contains a metal which catalyzes an undesirable side reaction that reduces the conversion of the monoethanolamine substrate (I) or N-(2-hydroxyethyl)glycine intermediate (III). A copper coating is also preferred if, for example, a non-copper metal in the catalyst is vulnerable to attack under the reaction conditions to an extent which significantly reduces the lifetime of the catalyst absent a copper-containing coating. Metals which are often vulnerable to such attack under alkaline or chelating reaction conditions include zinc, tin, cobalt, and iron.

d. Optional Modifier Metal

The dehydrogenation catalyst may optionally contain one or more supplemental metals (i.e., modifier metals) selected from the group consisting of chromium, titanium, niobium, tantalum, zirconium, vanadium, molybdenum, manganese, tungsten, cobalt, nickel, bismuth, tin, antimony, lead, and germanium. The presence of such a metal(s) tends to extend the life of the catalyst, i.e., increase the number of reaction runs in which the catalyst can be used before its activity decreases to unacceptable levels. Of the above elements, vanadium, chromium, molybdenum, and combinations thereof (especially chromium and molybdenum) are particularly preferred.

The amount of the modifier metal(s) can vary within wide limits. Preferably, the total concentration of modifier metals is at least about 10 parts per million parts of copper in the catalyst by weight. More preferably, the total concentration of the modifier metals in the catalyst is from about 0.002% to about 5% by weight, more preferably from about 0.002% to about 2.5% by weight, even more preferably from about 0.005% to about 2% by weight, and still even more preferably from about 0.5% to about 1.5% by weight. Typically, the total concentration of modifier metals does not exceed about 5% by weight. Although greater concentrations of modifier metals can be used, no additional benefits are usually obtained by exceeding such a concentration and the activity of the catalyst is generally reduced.

The modifier metal(s) may be contained in the metal support and/or in the catalyst active phase on the surface of the support. Where it is desirable to include the modifier metal(s) in an alloy-metal support, the modifier metal(s) are preferably incorporated into the alloy at the time the alloy is formed. Where it is desirable to include the modifier metal(s) in the catalyst active phase on the surface of the support, the modifier metal may, in some instances, be deposited simultaneously with the copper. Where, however, the copper is deposited via displacement deposition or electroless plating (discussed above), the modifier metal(s) are preferably added to the catalyst after the copper has been deposited because the modifier metals tend to dissolve under displacement deposition conditions and to inhibit electroless plating. A modifier metal(s) may typically be added to the catalyst surface by simply contacting the catalyst with an aqueous solution containing a salt (e.g., a sulfate, nitrate, chloride, etc.) of the modifier metal(s).

D. Concurrent Dehydrogenation-Hydrolysis (Method 2)

Concurrent dehydrogenation and hydrolysis of the N-cyanomethylated monoethanolamine intermediate (II) (Method 2) comprises contacting the N-cyanomethylated monoethanolamine intermediate (II), a metal-containing catalyst, water, and typically a hydroxide source.

Preferably at least about 2 molar equivalents (more preferably from about 2 to about 4 molar equivalents) of hydroxide source are introduced to the dehydrogenation/hydrolysis reaction zone per mole of the N-cyanomethylated monoethanolamine intermediate (II). The remaining reaction conditions (e.g., the types of suitable hydroxide sources, metal-containing catalysts, catalyst loading, temperature, pressure, reactor type, etc.) are the same as those described above for the dehydrogenation reaction (i.e., Method 1B).

E. Continuous Process for Making Iminodiacetic Acid Compounds (IV)

The present process (or any reaction step of the process) may be conducted in batch reactors, continuous reactors, or semicontinuous reactors. In a "batch reactor," all the reactants are added, and the reaction is allowed to proceed to completion (or a desired stopping point), after which the product is withdrawn. In a "continuous reactor," the reactants are continuously introduced and the products are simultaneously continuously withdrawn. In a "semicontinuous reactor," the reactor is charged with some of the reactants at the beginning, and the remaining reactants are fed continuously as the reaction progresses.

Figure 2:
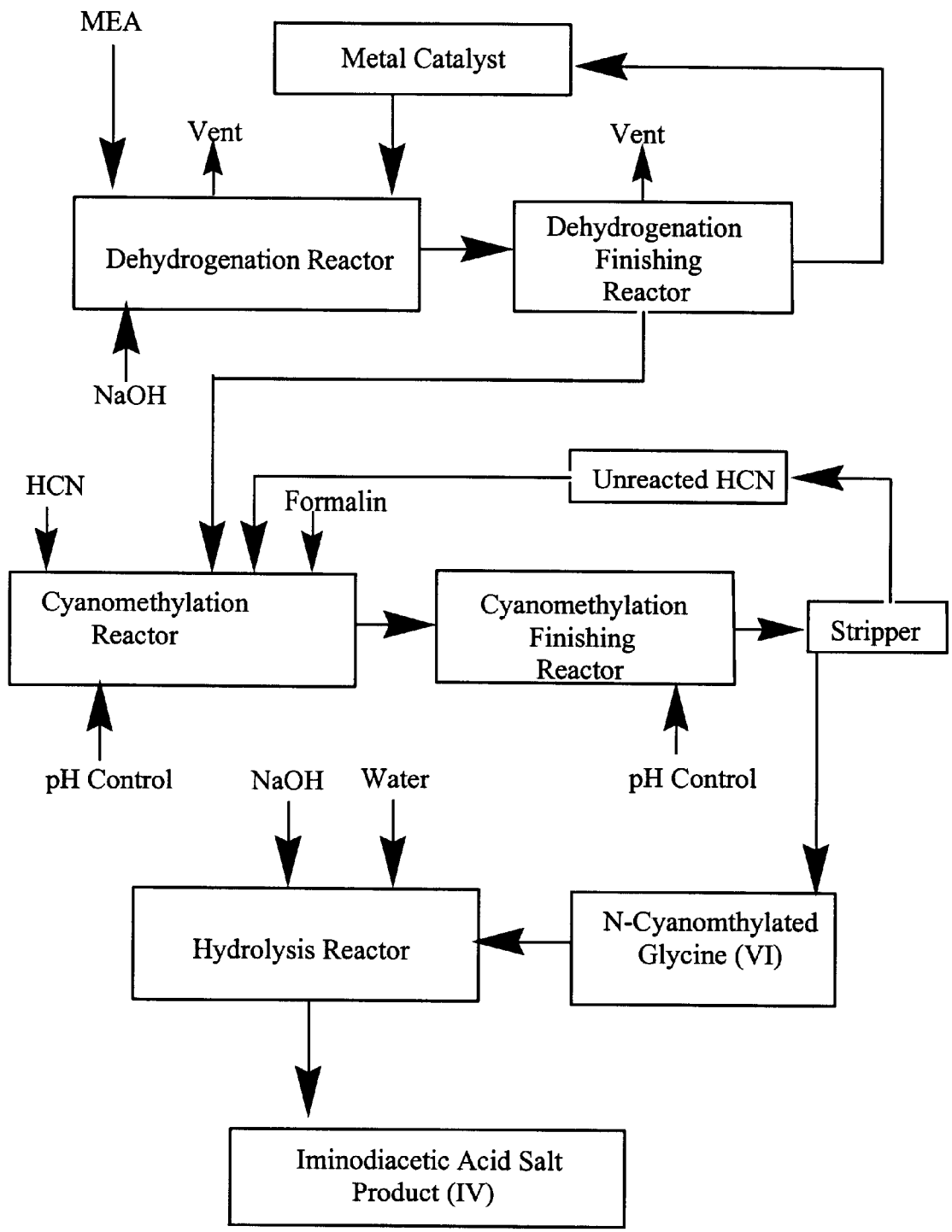
FIG. 2 shows a preferred embodiment for continuously making an iminodiacetic acid salt product from monoethanolamine, wherein the reaction is commenced in a dehydrogenation reaction zone.

The present invention can be advantageously conducted in a continuous reactor system comprising, for example, multiple stirred-tank reactors in series. A preferred embodiment of such a continuous process is shown in FIG. 1. An alternative preferred embodiment of such a continuous process is shown in FIG. 2. In both FIGS. 1 and 2, the reactants and steps are specifically identified for illustrative purposes and for convenience of discussion as abbreviations: 2-aminoethanol (monoethanolamine, MEA) is used as an example of the monoethanolamine substrate (I), formalin is the formaldehyde source, hydrogen cyanide (HCN) is the cyanide source, and NaOH is the hydroxide source. It should be recognized that in the embodiments shown in FIGS. 1 and 2, each of the feed streams could be introduced intermittently or continuously, with continuous introduction typically being more preferred. Likewise, each of the exit streams could be withdrawn from their respective reactors either intermittently or continuously, with continuous withdrawal typically being more preferred.

Referring to FIG. 1, an iminodiacetic acid salt product (IV) (specifically, disodium iminodiacetic acid) is formed in a continuous reactor system in which there are 3 reaction zones in series. In their respective order, the reaction zones comprise a cyanomethylation reaction zone, a hydrolysis reaction zone, and a dehydrogenation reaction zone. Each of these reaction zones preferably comprises at least one stirred-tank reactor. The preferred embodiment shown in FIG. 1 further includes additional units comprising a cyanomethylation finishing reactor, a stripper, and a dehydrogenation finishing reactor to enhance the overall operation of the basic system.

As shown in FIG. 1, the cyanomethylation of 2-aminoethanol (I) is preferably conducted, at least in part, in a stirred-tank reactor (equipped with pH control) under the cyanomethylation reaction conditions discussed above. The stirred-tank reactor preferably comprises a separate feed source for continuously supplying the 2-aminoethanol (I), HCN and formalin reactants, as well as a separate feed source for pH control (the pH control unit is preferably capable of providing separate supplies of a suitable acid and a suitable base to maintain a desired pH range). The 2-aminoethanol (I), HCN, and formalin react to form a reaction mixture comprising N-cyanomethylated 2-aminoethanol (II). A fraction of the reaction mixture is continuously withdrawn from the cyanomethylation reactor as an effluent. This effluent, in turn, is supplied to a cyanomethylation finishing reactor.

It should be recognized that the cyanomethylation reactor could optionally be initially charged with 2-aminoethanol (I), HCN, and formalin, followed by a continuous feed of 2-aminoethanol (I), HCN, and formalin. In that instance, a fraction of the reaction mixture is continuously withdrawn from the cyanomethylation reactor after the reaction has first been allowed to run for a period of time. The same concept also normally applies to all the reactors shown in FIGS. 1 and 2 into which multiple streams of different reactants are fed.

Typically, the cyanomethylation finishing reactor continuously receives the effluent from the cyanomethylation reactor. The optimum size of the reactor and the optimum residence time for further completion of the reaction can be readily determined from the teachings herein. After allowing the reaction to complete for a period of time, a fraction of the reaction mixture is withdrawn from the cyanomethylation finishing reactor as an effluent on a continuous basis to supply the stripper.

The stripper is preferably a vacuum vessel in which unreacted HCN, water, and 2-aminoethanol (I) are continuously separated from the N-cyanomethylated monoethanolamine product (II). The continuously separated HCN, water, and 2-aminoethanol (I) can optionally be returned (at least in part) to the cyanomethylation reactor or sent to a suitable waste disposal system. The stripped N-cyanomethylated monoethanolamine (II), on the other hand, is preferably continuously sent to a holding tank in which an inventory is maintained and from which a hydrolysis reactor can continuously be supplied.

In the embodiment shown in FIG. 1, the hydrolysis of the N-cyanomethylated monoethanolamine (II) is preferably conducted in a stirred-tank reactor using the reaction conditions discussed above for a hydrolysis reaction. The stirred-tank reactor in this embodiment is supplied continuously with N-cyanomethylated monoethanolamine (II), aqueous NaOH from a separate feed source, and optionally water from another feed source. The amount of NaOH supplied is normally from about 1.0 to about 3.0 times the rate at which N-cyanomethylated monoethanolamine (II) is supplied (on a molar equivalent basis). Preferably, the NaOH is supplied at from about 2.0 to about 2.2 times the rate at which N-cyanomethylated monoethanolamine (II) is supplied (on a molar equivalent basis). Use of from about 2.0 to about 2.2 times the molar equivalent of NaOH compared to N-cyanomethylated monoethanolamine (II) normally provides for greater rates of hydrolysis, and also supplies the NaOH for the subsequent dehydrogenation of the N-cyanomethylated monoethanolamine hydrolysate. The continuously supplied N-cyanomethylated monoethanolamine (II), NaOH, and water react in the hydrolysis reactor to form sodium N-(2-hydroxyethyl)glycinate (III). A fraction of the hydrolysis reaction mixture is preferably continuously withdrawn from the hydrolysis reactor as an effluent, which is supplied to the dehydrogenation reactor. While complete hydrolysis is preferable, less than complete hydrolysis is normally acceptable because the downstream reaction conditions in the dehydrogenation reactor and dehydrogenation finishing reactor subsequent to the hydrolysis reactor are usually suitable to fully complete the hydrolysis.

The partially to completely hydrolyzed effluent from the hydrolysis reactor is continuously transferred to the dehydrogenation reactor to produce the disodium iminodiacetic acid product (IV) using the reaction conditions described above for a dehydrogenation. The dehydrogenation reactor is preferably supplied continuously with the sodium N-(2-hydroxyethyl)glycinate (III) from the hydrolysis reactor, a metal-containing catalyst from a catalyst feed source, and optionally aqueous NaOH from a separate feed source. Addition of NaOH on a continuous basis is preferable whenever less than 2 molar equivalents of NaOH are added per each equivalent of N-cyanomethyl monoethanolamine (II) in the hydrolysis reactor. After the continuously supplied sodium N-(2-hydroxyethyl)glycinate (III), metal-containing catalyst, and, optionally, NaOH are contacted to form the disodium iminodiacetic acid (IV), a fraction of the dehydrogenation reaction mixture is preferably continuously withdrawn from the dehydrogenation reactor as an effluent which is supplied to a dehydrogenation finishing reactor.

The dehydrogenation finishing reactor preferably continuously receives the effluent from the dehydrogenation reactor. The optimum size of the reaction and the optimum residence time for further completion of the reaction can be readily determined from the teachings herein. After allowing a period for the reaction to complete to the desired level, the aqueous mixture of disodium iminodiacetic acid (IV) is preferably separated from the metal-containing catalyst. The separated metal-containing catalyst can be recycled, either partially or completely, to the catalyst feed source from which catalyst is supplied back to the dehydrogenation reactor.

Referring to FIG. 2, an iminodiacetic acid salt product (IV) (specifically, disodium iminodiacetic acid) is formed in a continuous reactor system in which there are 3 reaction zones in series in the following order: a dehydrogenation reaction zone, a cyanomethylation reaction zone, and a hydrolysis reaction zone. In the preferred embodiment shown in FIG. 2, the reactor system further comprises a dehydrogenation finishing reactor, a cyanomethylation finishing reactor, and a stripper to enhance the overall operation of the basic continuous 3-reactor system.

In the embodiment shown in FIG. 2, 2-aminoethanol (I) preferably is continuously conveyed to the dehydrogenation reaction zone to form sodium glycinate (V) using the reaction conditions discussed above for a dehydrogenation. The dehydrogenation reactor is supplied continuously with (a) the 2-aminoethanol (I), (b) a metal-containing catalyst from a catalyst feed source, and (c) typically, NaOH. The continuously supplied 2-aminoethanol (I) reacts in the presence of the metal-containing catalyst and NaOH to form sodium glycinate (V). A fraction of the dehydrogenation reaction mixture is preferably continuously withdrawn from the dehydrogenation reactor as an effluent, which, in turn, is supplied to a dehydrogenation finishing reactor.

The dehydrogenation finishing reactor preferably continuously receives the effluent from the dehydrogenation reactor. The optimum size of the reaction and the optimum residence time for further completion of the reaction can be readily determined from the teachings herein. After allowing a period for the reaction to complete to the desired level, the aqueous mixture of sodium glycinate (V) is preferably separated from the metal-containing catalyst. At least a portion of the separated metal-containing catalyst can subsequently be recycled to the catalyst feed source from which metal-containing catalyst may again be supplied to the dehydrogenation reactor.

Cyanomethylation of the sodium glycinate (V) preferably is conducted in a stirred-tank cyanomethylation reactor (equipped with pH control) using the reaction conditions discussed above for a cyanomethylation. The cyanomethylation reactor is preferably supplied continuously with the effluent from the dehydrogenation finishing reactor, along with sources for HCN, formalin, and pH control. The pH control unit preferably operates as described for FIG. 1. The continuously supplied sodium glycinate (V), HCN, and formalin continuously react to form a sodium N-cyanomethylated glycinate (VI). A fraction of the reaction mixture is preferably continuously withdrawn from the cyanomethylation reactor as an effluent, which, in turn, is supplied to the cyanomethylation finishing reactor.

The cyanomethylation finishing reactor preferably continuously receives the effluent from the cyanomethylation reactor and operates as described above for the cyanomethylation reactor in FIG. 1. A fraction of the reaction mixture is withdrawn from the cyanomethylation finishing reactor as an effluent on a continuous basis to supply the stripper.

As with FIG. 1, the stripper preferably is a vacuum vessel. In this stripper, unreacted HCN and water are continuously removed from the sodium N-cyanomethylated glycinate (VI). The continuously removed HCN and water can be optionally returned (at least in part) to the cyanomethylation reactor or sent to a suitable waste disposal system. The stripped sodium N-cyanomethylated glycinate (VI) is preferably continuously sent to a holding tank in which an inventory is maintained and from which the hydrolysis reaction zone can be continuously supplied.

Hydrolysis of the sodium N-cyanomethylated glycinate (VI) is preferably conducted in a stirred-tank hydrolysis reactor using the reaction conditions discussed above for a hydrolysis reaction. The stirred-tank hydrolysis reactor in this embodiment is preferably continuously supplied with (a) the sodium N-cyanomethylated glycinate (VI), (b) NaOH, and (c) optionally water from another feed source. The NaOH preferably is fed at a rate of at least 1.0 to about 3.0 (more preferably from 1.0 to about 1.2) times the rate at which sodium N-cyanomethylated glycinate (VI) is supplied on a molar equivalent basis. The continuously supplied sodium N-cyanomethylated glycinate (VI) reacts in the presence of the NaOH to form the disodium iminodiacetic acid product (IV). A fraction of the resulting hydrolysis reaction mixture is continuously withdrawn from the hydrolysis reactor to recover the product.

F. Use of Iminodiacetic Acid Compounds to make N-(Phosphonomethyl)Glycine and Salts Thereof Various iminodiacetic acid compounds (preferably alkali metal salts of iminodiacetic acid, and even more preferably a sodium salt of iminodiacetic acid) produced by this invention may be used as raw materials to prepare N-(phosphonomethyl)glycine and agronomically acceptable salts thereof in accordance with many well-known methods in the art. As used herein, an "agronomically acceptable salt" is defined as a salt which contains a cation(s) that allows agriculturally and economically useful herbicidal activity of an N-(phosphonomethyl)glycine anion. Such a cation may be, for example, an alkali metal cation (e.g., a Na ion), an ammonium ion, an isopropyl ammonium ion, a tetraalkylammonium ion, a trialkyl sulfonium ion, a protonated primary amine, a protonated secondary amine, or a protonated tertiary amine.

Salts of iminodiacetic acid, for example, may be phosphonomethylated in a reaction zone containing HCl, phosphorous acid ($H_3PO_3$), and formaldehyde ($CH_2O$) to form N-(phosphonomethyl)iminodiacetic acid. See, e.g., Gentilcore, U.S. Pat. No. 4,775,498 (also reporting that the HCl and $H_3PO_3$ may optionally be formed by adding $PCl_3$ to water). The N-(phosphonomethyl)iminodiacetic acid may, in turn, be contacted with oxygen in the presence of a catalyst to oxidatively cleave a carboxymethyl group to form N-(phosphonomethyl)glycine. Many catalysts are known in the art for conducting this dehydrogenation, and include, for example, carbon catalysts (see, e.g., Hershman, U.S. Pat. No. 3,969,398; and Chou, U.S. Pat. Nos. 4,624,937 and 4,696,772); a carbon catalyst along with a noble metal co-catalyst supported on aluminosilicate (see, e.g., Felthouse, U.S. Pat. No. 4,582,650), and catalysts comprising a noble metal supported on carbon (see, e.g., Franz, U.S. Pat. No. 3,950,402; Ramon et al., U.S. Pat. No. 5,179,228; and Ebner et al., PCT/US99/03402). See also, Franz, et al., *Glyphosate: A Unique Global Herbicide* (ACS Monograph 189, 1997) at pp. 233–62 (disclosing the use of iminodiacetic acid compounds as raw materials to form N-(phosphonomethyl)glycine).

VI. Definitions

The following definitions are provided in order to aid the reader in understanding the detailed description of the present invention:

"GC" means gas chromatography.

"HPLC" means high pressure liquid chromatography.

"IC" means ion chromatography.

"NMR" means nuclear magnetic resonance spectroscopy.

"MS" means mass spectrometry.

VII. EXAMPLES

These examples merely further illustrate and explain Applicants' invention. Applicants' invention should not be considered to be limited to any of the details in these examples.

In these examples, compound numbers in Roman numerals reflect the structures which appear in Reaction Schemes 1 and 2, and FIGS. 1 and 2. The example reactions were monitored for extent of reaction, and reactants, intermediates, by-products, and products were quantified by HPLC analysis with UV absorption detection at 210 nm and by NMR.

Example 1

Making Disodium Iminodiacetic Acid in 3 steps, Beginning With the Cyanomethylation of 2-aminoethanol with Glycolonitrile 2-aminoethanol (9 g; 0.15 mol) was introduced into a 100 ml round-bottom flask (3 neck, 14/20 joints) containing a magnetic stirrer and fitted with a 60 ml addition funnel and an adapter for $N_2$. The mixture was stirred and cooled in an ice bath to 2° C. An aqueous solution of glycolonitrile ($HOCH_2CN$) (50% by weight; 17 g; 0.15 mol) was added dropwise over 10 minutes during which the temperature in the reactor never exceeded 14° C. After stirring in the ice bath for 15 minutes, the reaction was allowed to warm to room temperature and stirred for an additional 2 hours. Analysis by NMR indicated that the reaction was complete with a solution of 2-(N-cyanomethylamino)ethanol being formed.

The 2-(N-cyanomethylamino)ethanol solution prepared above was placed into a 100 ml Hastelloy-C autoclave. A warm (about 60° C.) aqueous solution of NaOH (50% by weight; 30.0 g; 0.375 mol) was carefully added, during which time $NH_3$ rapidly evolved. HPLC analysis confirmed the presence of N-(2-hydroxyethyl)glycine in the solution.

A slurry containing copper sponge (3.57 g) in water (about 10 ml) was added to the N-(2-hydroxyethyl)glycine solution. The sealed autoclave was purged 5 times with $H_2$ (200 psia), pressurized to 135 psia with $H_2$, and then heated at 160° C. for 5 hours, during which time the evolved $H_2$ was vented using a back-pressure regulator to maintain a pressure of 135 psia. The reaction mixture was then filtered and analyzed by HPLC, which showed a 38% yield of disodium iminodiacetate (based on the starting 2-aminoethanol).

Example 2
Making Disodium Iminodiacetic Acid in 3 Separate Steps Starting with 2-aminoethanol, HCN, and Formalin In this experiment, HCN was generated in situ in a reaction mixture from NaCN and $H_2SO_4$ for ease of handling and safety. 2-aminoethanol (9 g; 0.15 mol) was introduced into a 100 ml round-bottom flask (3 neck, 14/20 joints) containing a magnetic stirrer and fitted with a 60 ml addition funnel and an adapter for $N_2$. Aqueous sulfuric acid (50% by weight; 11.1 g; 0.10 mol) was then introduced into the flask. The resulting mixture was stirred and cooled in an ice bath to 2° C. Sodium cyanide (9.8 g; 0.20 mol) in water (20 ml) was then added dropwise, during which time the temperature in the reactor was kept below 5° C. Subsequently, formalin (37%; 10.3 g; 0.15 mol) was added dropwise, with the temperature of the reactor again being kept below 5° C. After stirring in the ice bath for 15 minutes, the reaction mixture was allowed to warm to room temperature and then stirred for an additional 2 hours. Analysis by NMR confirmed that the reaction was complete, with a solution of 2-(N-cyanomethylamino)ethanol being formed. The reaction mixture was then stripped at room temperature overnight under vacuum (1–2 mm Hg) to remove excess 2-aminoethanol and HCN.

The 2-(N-cyanomethylamino)ethanol was next dissolved in water (20 ml) and placed into a 100 ml Hastelloy-C autoclave. A warm (about 60° C.) aqueous solution of NaOH (50% by weight; 30.0 g; 0.375 mol) was carefully added, during which time $NH_3$ was rapidly evolved. HPLC analysis confirmed the presence of N-(2-hydroxyethyl)glycine in the resulting solution.

A slurry of copper sponge (3.57 g) in water (about 10 ml) was then added to the N-(2-hydroxyethyl)glycine solution. The sealed autoclave was purged 5 times with $H_2$ (200 psia), pressurized to 135 psia with $H_2$, and then heated at 160° C. for 5 hours, during which time the evolved $H_2$ was vented using a back-pressure regulator to maintain a pressure of 135 psia. The reaction mixture was then filtered and analyzed by HPLC to confirm the formation of disodium iminodiacetate.

Example 3
Making Disodium Iminodiacetic Acid Starting with 2-aminoethanol and Excess Glycolonitrile Under Conditions which Tend to Reduce the Formation of Undesirable Byproducts This example shows the preparation of the disodium salt of iminodiacetic acid, starting with 2-aminoethanol and a 7% molar excess of glycolonitrile using conditions which tend to increase the yield of N-(2-hydroxyethyl)glycine and reduce the amount of N-(2-hydroxyethyl)iminodiacetic acid during the cyanomethylation and hydrolysis steps.

2-aminoethanol (10.6 g; 0.174 mol) was introduced into a 100 ml round-bottom flask (3 neck, 14/20 joints) containing a magnetic stirrer and fitted with a 60 ml addition funnel and an adapter for $N_2$. The mixture was stirred and cooled in an ice bath to 2° C. Glycolonitrile (53%; 17.5 g; 0.162 mol) was added dropwise over 18 minutes, during which time the temperature in the reactor increased to 10.4° C. The reaction mixture was maintained in the ice bath for 34 minutes, at which time the temperature was about 1° C. The mixture was then removed from the ice bath. The reaction mixture temperature was increased to 32° C. over 23 minutes, and then cooled to ambient temperature. After stirring the mixture in the ice bath for 15 minutes, the reaction was allowed to warm to room temperature, and then stirred for an additional 2 hours. Afterward, the reaction mixture was stripped at room temperature overnight under vacuum (1–2 mm Hg) to remove excess 2-aminoethanol and HCN. There was essentially no color to the reaction mixture. After stripping the crude reaction product (18 g), proton NMR analysis indicated that the reaction was essentially complete, although some by-product resonances were present.

The crude 2-(N-cyanomethylamino)ethanol prepared above was next dissolved in water (20 ml). The solution was cooled to 7–8° C. in an ice bath, and then an aqueous solution of NaOH (50% by weight; 15 g) was added dropwise over a 5 minute period. The temperature of the reaction mixture increased to 11° C., and then cooled to 6° C. After an additional 5 minutes, the mixture was removed from the bath and allowed to warm to ambient temperature. The temperature slowly rose to 57° C. over 38 minutes, and then dropped to 44° C. after 57 minutes. After 2 hours, the slightly orange reaction mixture was at ambient temperature. Results of proton NMR indicated complete reaction to N-(2-hydroxyethyl)glycine. The crude product weighed 53.2 g. Analysis of a portion by HPLC showed a N-(2-hydroxyethyl)-glycine yield of 93.4% (based on 2-aminoethanol), a residual 2-aminoethanol yield of 5.67%, and a N-(2-hydroxyethyl)iminodiacetic acid yield of 0.93% yield. The acids were present as the sodium salts.

The N-(2-hydroxyethyl)glycine sodium salt, residual 2-aminoethanol, and disodium N-(2-hydroxyethyl)-iminodiacetate were transferred with the aid of deionized water into a 300 ml nickel autoclave. A slurry of copper sponge (7.2 g) in water (about 20 ml) was added to the hydrolyzed 2-(N-cyanomethylamino)ethanol solution, after which an aqueous solution of NaOH (50%; 15 g) was added. The sealed and stirred autoclave was purged 5 times with $H_2$ (200 psia) and pressurized to 135 psia with $H_2$. The reaction mixture was then heated at 160° C. for 7 hours, during which time the evolved $H_2$ was vented using a back-pressure regulator to maintain a pressure of 135 psia. The reaction mixture was then filtered and analyzed by HPLC to confirm the formation of disodium iminodiacetate, and detect any trisodium nitrilotriacetate in the mixture.

Example 4
Making Disodium Iminodiacetic Acid by Cyanomethylating 2-aminoethanol with Glycolonitrile, and then Concurrently Hydrolyzing and Dehydrogenating the 2-(N-cyanomethylamino)-ethanol Intermediate 2-aminoethanol (9 g; 0.15 mol) was introduced into a 100 ml round-bottom flask (3 neck, 14/20 joints) containing a magnetic stirrer and fitted with a 60 ml addition funnel and an adapter for $N_2$. The mixture was stirred and cooled in an ice bath to 2° C. Glycolonitrile (50%; 17 g; 0.15 mol) was added dropwise over 10 minutes, during which the temperature in the reactor never exceeded 14° C. After stirring in the ice bath for 15 minutes, the reaction was allowed to warm to room temperature and then stirred for an additional 2 hours. NMR analysis indicated that the reaction was complete, forming a solution of 2-(N-cyanomethylamino) ethanol.

The 2-(N-cyanomethylamino)ethanol solution prepared above was placed into a 100 ml Hastelloy-C autoclave. A slurry of copper sponge (3.57 g) in water (about 10 ml) was added to the 2-(N-cyanomethylamino)ethanol solution. The sealed autoclave was purged 5 times with $H_2$ (200 psia) and pressurized to 135 psia with $H_2$. A warm (about 60° C.) aqueous solution of NaOH (50% by weight; 30.0 g; 0.375 mol) was carefully added, and then the mixture was heated at 160° C. for 5 hours, during which time the evolved $H_2$ and

Example 5
Making Disodium Iminodiacetic Acid by Cyanomethylating 2-aminoethanol with HCN and Formalin, and then Concurrently Hydrolyzing and Dehydrogenating the 2-(N-cyanomethylamino)-ethanol Intermediate For ease of handling and safety, HCN was generated in situ in the reaction mixture from sodium cyanide and $H_2SO_4$.

2-aminoethanol (9 g; 0.15 mol) was transferred into a 100 ml round-bottom flask (3 neck, 14/20 joints) containing a magnetic stirrer and fitted with a 60 ml addition funnel and an adapter for $N_2$. Aqueous sulfuric acid (50%; 11.1 g; 0.10 mol) was then introduced into the flask. The mixture was stirred and cooled in an ice bath to 2° C. An aqueous solution of sodium cyanide (9.8 g; 0.20 mol) in water (20 ml) was added dropwise while keeping the temperature in the reactor below 5° C. Formalin (37%; 10.3 g; 0.15 mol) was then added dropwise, again keeping the temperature in the reactor below 5° C. After stirring in the ice bath for 15 minutes, the reaction was allowed to warm to room temperature and then stirred for an additional 2 hours. NMR analysis indicated that the reaction was complete, forming a solution of 2-(N-cyanomethyl-amino)ethanol. The reaction mixture was then stripped at room temperature overnight under vacuum (1–2 mm Hg) to remove excess 2-aminoethanol and HCN.

The 2-(N-cyanomethylamino)ethanol prepared above was dissolved in water (20 ml) and then placed into a 100 ml Hastelloy-C autoclave. A slurry of copper sponge (3.57 g) in water (about 10 ml) was added to the 2-(N-cyanomethyl-amino)ethanol solution. The sealed autoclave was purged 5 times with $H_2$ (200 psia) and pressurized to 135 psia with $H_2$. A warm (about 60° C.) aqueous solution of NaOH (50% by weight; 30.0 g; 0.375 mol) was carefully added, and then the mixture was heated at 160° C. for 5 hours, during which time the evolved $H_2$ and $NH_3$ were vented using a back-pressure regulator to maintain a pressure of 135 psia. The reaction mixture was then filtered and analyzed by HPLC to confirm the presence of disodium iminodiacetate.

Example 6
Making Disodium Iminodiacetic Acid Starting with Glycine and Glycolonitrile Glycine (7.4 g) and deionized water (15 ml) were introduced into a 100 ml beaker, followed by NaOH (50% by weight, 7.92 g). The resulting sodium glycinate solution was then introduced into a 100 ml, 3-necked, round-bottom flask containing a magnetic stir bar and fitted with a thermocouple, a 60 ml addition funnel, and an $N_2$ inlet adapter. Additional deionized water (11 ml) was added, and the solution cooled in an ice bath to about 5° C. Glycolonitrile (53%; 10.7 g) was added dropwise to the reaction mixture over about 1 minute. After 5 minutes, the reaction mixture was removed from the ice bath, and allowed to warm to ambient temperature. After 2 hours, the non-colored reaction mixture was analyzed by NMR of a sample obtained by diluting an aliquot into deuterium oxide. Results of the spectral analysis indicated that the glycine was almost completely converted to sodium N-cyanomethylglycinate. The pH of the reaction mixture was 10.6 at 24.6° C.

The sodium N-cyanomethylglycinate solution was returned to the ice bath and cooled to 5–10° C. Sodium hydroxide (50%; 8.6 g) was added dropwise over about 30 seconds, and the temperature was allowed to rise to 33° C. over about 10 minutes, during which time the reaction mixture changed from colorless to light yellow. The reaction mixture was cooled to 22° C. in the ice bath. After about 10 minutes, the reaction mixture was removed from the ice bath, and stirred at room temperature overnight. A short path with a Vigreux distillation head was added to the 100 ml round-bottom flask, and the addition funnel was removed. The reaction mixture was heated to 95° C. at a pressure of 400 mm Hg, and water was distilled over at 85° C. After 45 minutes, the distillation was stopped, and the crude product weighed 32.4 g. The distillate weighed 16.3 g. By the end of the stripping, the crude product had changed from yellow to orange. The product solidified quickly and was analyzed by liquid chromatography. The analysis showed by weight disodium iminodiacetate (47.35%), trisodium nitriloacetic acid (1.52%), sodium glycolate (3.76%), sodium glycinate (1.09%), and disodium N-(carboxamidomethyl) iminodiacetate (1.92%). The reaction yielded, based on starting glycine, 86% of the expected disodium iminodiacetate.

Example 7
Making Disodium Iminodiacetic Acid from Glycine and (a) Formalin and HCN, or (b) Glycolonitrile For ease of handling and safety, HCN is generated in situ in the reaction mixture from NaCN and $H_2SO_4$.

Using the process described in Example 1 of Goto et al.'s U.S. Pat. No. 4,782,183, 2-aminoethanol is contacted with aqueous NaOH and copper sponge to form 9.8 grams of sodium glycinate in 20 ml of water.

The sodium glycinate solution is introduced into a 100 ml, 3-necked, round-bottom flask containing a magnetic stir bar and fitted with a thermocouple, a 60 ml addition funnel, and an $N_2$ inlet adapter. Sulfuric acid (50%; 7.4 g; 0.67 mol) is then introduced, and the solution is cooled in an ice bath to about 5° C. Sodium cyanide (7.5 g; 0.15 mol) in 10 ml water is introduced dropwise while the temperature is maintained at less than 5° C. Formalin (37%; 6.9 g; 0.10 mol) is then added dropwise to the reaction mixture, again while maintaining the temperature at less than 5° C. After 5 minutes, the mixture is removed from the ice bath. The reaction mixture is allowed to warm to ambient temperature. After 2 hours, spectral analysis is used to ensure completion of the reaction and the formation of sodium N-cyanomethyl-glycinate. The sodium N-cyanomethylglycinate solution is returned to the ice bath and cooled to 5–10° C. Sodium hydroxide (50%; 8.6 g) is added dropwise over about 30 seconds, and the temperature is allowed to increase to 33° C. over about 10 minutes. The reaction mixture is then cooled to 22° C. After about 10 minutes, the reaction mixture is removed from the ice bath, and stirred at room temperature overnight. The reaction mixture is subsequently heated to 95° C. at a pressure of 400 mm Hg, and water is distilled over at 85° C. After 45 minutes, the distillation is stopped, and the crude product weighed. Liquid chromatography analysis is used to confirm the formation of disodium iminodiacetate.

The above process is repeated except that glycolonitrile (53%; 10.7 g) is used as the formaldehyde and cyanide source, rather than formalin and HCN.

Example 8
Making Disodium Iminodiacetic Acid from 2-aminoethanol and Glycolonitrile using a Continuous Process having 3 Reactors, Beginning with a Cyanomethylation Reactor The first reactor in the continuous reactor system was a 1000 ml, 3-necked, round-bottom flask containing a magnetic stirrer and fitted with an adapter for $N_2$. The flask was cooled in an ice bath at 2° C. 2-aminoethanol was pumped into the stirred flask at a rate of 1.9 g/min, while simultaneously pumping 53% glycolonitrile into the flask at a rate of 1.7 g/min.

After 1 hour (and the addition of 216.9 g of reactants), the cyanomethylation reaction mixture was continuously pumped at 2.9 g/min to a hydrolysis reactor. The hydrolysis reactor was a 2000 ml, 3-necked, round-bottom flask containing a magnetic stirrer and fitted with an adapter for the $N_2$ sweep. With the flask at ambient temperature, 10% NaOH was pumped continuously into the stirred hydrolysis reactor at a rate of 2.9 g/ml. Samples were taken from the hydrolysis reactor at 0.5, 1.0, 3.5, 5.5, and 6.0 hr, and analyzed by HPLC. Results are summarized in Table 1.

TABLE 1

Results summary from a Continuous Cyanomethylation and Hydrolysis Reaction

| Compound | Hydrolysis Time (hr) | 0.5 | 1.0 | 3.5 | 5.5 | 6.0 |
|---|---|---|---|---|---|---|
| MEA | % Yield | 1.94 | 1.85 | 2.19 | 1.12 | 1.11 |
| HEG | % Yield | 65.2 | 46.4 | 68.1 | 65.7 | 78.7 |
| HEIDA | % Yield | 14.7 | 14.9 | 12.8 | 7.4 | 8.1 |
| Glycolic Acid | % Yield | 0.57 | 0.55 | 0.86 | 0.71 | 0.71 |
| Formic Acid | % Yield | 0.37 | 0.38 | 0.30 | 0.25 | 0.34 |
|  | Closure | 81.8 | 63.1 | 83.1 | 74.2 | 87.9 |

MEA is 2-aminoethanol; HEG is N-(2-hydroxyethyl)glycine; HEIDA is N-(2-hydroxyethyl)iminodiacetic acid; Closure is the material balance in % or the total amount of product, by-products, and starting materials.

After 6 hours, pumping of the reaction mixture from the hydrolysis reactor and into a dehydrogenation reactor is started at a rate of 2.9 g/min. The dehydrogenation reactor is a 3000 ml nickel autoclave. The dehydrogenation reactor contains 200 g of an anchored metal catalyst (i.e., copper on platinum on activated carbon, such that the catalyst contains 13.4 wt % copper and 3.4 wt % platinum). The nickel autoclave is maintained at from 155–165° C. and 135 psia after purging 5 times with 200 psia $N_2$. In addition to the hydrolysis reaction mixture being fed at 2.9 g/min, 20% NaOH is also pumped continuously into the dehydrogenation reactor at a rate of 1.5 g/min. After 5 hours, the dehydrogenation reaction mixture is continuously withdrawn at a rate of 4.4 g/min and analyzed. Liquid chromatography analysis is used to confirm the presence of disodium iminodiacetic acid.

Example 9
Making Disodium Iminodiacetic Acid from 2-aminoethanol, HCN, and Formalin using a Continuous Process having 3 Reactors, Beginning with a Cyanomethylation Reactor The first reactor in this continuous reactor system is a 1000 ml, 3-necked, round-bottom flask containing a magnetic stirrer and fitted with an adapter for $N_2$. The flask is placed in a lethal service facility and cooled in an ice bath at 2° C. 2-aminoethanol is pumped into the stirred flask at a rate of 1.9 g/min, while simultaneously pumping into the flask 37% formalin at a rate of 2.6 g/min, and liquid HCN at a rate of 0.9 g/min.

After 2 hours (and the addition of 648 g of reactants), the cyanomethylation reaction mixture is continuously pumped at 5.4 g/min to a hydrolysis reactor. The hydrolysis reactor is a 5000 ml, 3-necked, round-bottom flask containing a magnetic stirrer and fitted with an adapter for the $N_2$ sweep. With the flask at ambient temperature, 20% NaOH is pumped continuously into the stirred hydrolysis reactor at a rate of 1.5 g/ml.

After 6 hours, pumping of the reaction mixture from the hydrolysis reactor into a dehydrogenation reactor is started at a rate of 6.9 g/min. The dehydrogenation reactor is a 3000 ml nickel autoclave. The dehydrogenation reactor contains 200 g of an anchored-metal catalyst (i e., copper on platinum on activated carbon, such that the catalyst contains 13.4 wt % copper and 3.4 wt % platinum). The nickel autoclave is maintained at 155–165° C. and 135 psia after purging 5 times with 200 psia $N_2$. In addition to the hydrolysis reaction mixture at 6.9 g/min, 20% NaOH is pumped continuously into the dehydrogenation reactor being fed at a rate of 1.5 g/min. After 5 hours, the dehydrogenation reaction mixture is continuously withdrawn at a rate of 8.4 g/min and analyzed with liquid chromatography to confirm the presence of disodium iminodiacetic acid.

Example 10
Making Disodium Iminodiacetic Acid from 2-aminoethanol, HCN, and Formalin using a Continuous Process having 2 Reactors, with one of the Reactors being used to Concurrently Hydrolyze and Dehydrogenate the N-cyanomethylated Monoethanolamine Intermediate The first reactor in this continuous reactor system is a 1000 ml, 3-necked, round-bottom flask containing a magnetic stirrer and fitted with an adapter for $N_2$. The flask is placed in a lethal service facility, and cooled in an ice bath at 2° C. 2-amino ethanol is pumped into the stirred flask at a rate of 1.9 g/min, while simultaneously pumping into the flask 37% formalin at a rate of 2.6 g/min, and liquid HCN at a rate of 0.9 g/min.

After 2 hours (and the addition of 648 g of reactants), the cyanomethylation reaction mixture is continuously pumped at 5.4 g/min to the hydrolysis/dehydrogenation reactor. The hydrolysis/dehydrogenation reactor is a 3000 ml nickel autoclave containing 200 g of an anchored-metal catalyst (i.e., copper on platinum on activated carbon, such that the catalyst contains 13.4 wt % copper and 3.4 wt % platinum). The nickel autoclave is maintained at 155–165° C. and 135 psia after purging 5 times with 200 psia $N_2$. In addition to the hydrolysis reaction mixture at 5.4 g/min, 20% NaOH is pumped continuously into the reactor being fed at a rate of 3.0 g/min. After 5 hours, the dehydrogenation reaction mixture is continuously withdrawn at a rate of 8.4 g/min, and analyzed with liquid chromatography to confirm the presence of disodium iminodiacetic acid.

Example 11
Making Disodium Iminodiacetic Acid from 2-aminoethanol, HCN, and Formalin in a Continuous Process Having Multiple Reactors in Series, Beginning with a Cyanomethylation Reaction Zone The first reactor in this continuous reactor system is a 500 ml, 3-necked, round-bottom flask containing a magnetic stirrer and fitted with an adapter for $N_2$. The flask is placed into a lethal service facility and cooled in an ice bath at 2° C. 2-aminoethanol is pumped into the stirred flask at a rate of 1.9 g/min, while simultaneously pumping into the flask 37% formalin at a rate of 2.6 g/min, and liquid HCN at a rate of 0.9 g/min.

After 1 hour (and the addition of 324 g of reactants), the cyanomethylation reaction mixture is continuously pumped at 5.4 g/min into the cyanomethylation finishing reactor. The cyanomethylation finishing reactor is a 500 ml, 3-necked, round-bottom flask containing a magnetic stirrer and fitted with an adapter for $N_2$. The flask is at ambient temperature.

After 1 hour (and the addition of 324 g of reactants), the cyanomethylation finishing reaction mixture (containing 2-(N-cyanomethylamino)ethanol) is continuously pumped at 5.4 g/min into a stripper. The stripper is a Teflon spinning band column operating at 100 mm Hg. The cyanomethylation finishing reactor mixture is introduced at the top of the stripper column. The 2-(N-cyanomethylamino)ethanol flows down the spinning column to a 50 ml receiver, concurrent with the removal of excess HCN and other volatiles at the top of the column.

The 2-(N-cyanomethylamino)ethanol mixture is next continuously pumped at 5.4 g/min into a hydrolysis reactor. The hydrolysis reactor is a 5000 ml, 3-necked, round-bottom flask containing a magnetic stirrer and fitted with an adapter for the $N_2$ sweep. With the flask at ambient temperature, 20% NaOH is pumped continuously into the hydrolysis reactor at a rate of 1.5 g/ml.

After 6 hours, pumping of the reaction mixture from the hydrolysis reactor to a dehydrogenation reactor is started at a rate of 6.9 g/min. The hydrolysis reactor is a 2000 ml nickel autoclave containing 200 g of an anchor metal catalyst (i.e., copper on platinum on activated carbon, such that the catalyst contains 13.4 wt % copper and 3.4 wt % platinum). The nickel autoclave is maintained at 155–165° C. and 135 psia after purging 5 times with 200 psia $N_2$. In addition to the hydrolysis reaction mixture being fed at 6.9 g/min, 20% NaOH is pumped continuously into the dehydrogenation reactor at a rate of 1.5 g/min.

After 2.5 hours, the dehydrogenation reaction mixture is continuously pumped at a rate of 8.4 g/min to a dehydrogenation finishing reactor, which is a 2000 ml nickel autoclave containing 200 g of an anchor-metal catalyst (i.e., copper on platinum on activated carbon, such that the catalyst contains 13.4 wt % copper and 3.4 wt % platinum). The nickel autoclave is maintained at 155–165° C. and 135 psia after purging 5 times with 200 psia $N_2$.

After 2.5 hours, the dehydrogenation finishing reaction mixture is continuously withdrawn at a rate of 8.4 g/min to a product vessel and analyzed via liquid chromatography to confirm the presence of disodium iminodiacetic acid.

Example 12

Making Disodium Iminodiacetic Acid from 2-aminoethanol, HCN, and Formalin in a Continuous Process Having Multiple Reactors in Series, Beginning with a Dehydrogenation Reaction Zone The first reactor in this continuous reactor system is a dehydrogenation reactor, which is a 2000 ml nickel autoclave containing 200 g of an anchor-metal catalyst (copper on platinum on activated carbon, such that the catalyst contains 13.4 wt % copper and 3.4 wt % platinum). The nickel autoclave is maintained at 155–165° C. and 135 psia after purging 5 times with 200 psia $N_2$. 2-aminoethanol is pumped into the dehydrogenation reactor at 1.9 g/min, while simultaneously pumping 40% NaOH into the reactor at a rate of 4.0 g/min.

After 2.5 hours, the dehydrogenation reaction mixture is continuously pumped at a rate of 5.9 g/min into a dehydrogenation finishing reactor, which is a 2000 ml nickel autoclave containing 200 g of an anchor-metal catalyst (i.e., copper on platinum on activated carbon, such that the catalyst contains 13.4 wt % copper and 3.4 wt % platinum). The nickel autoclave is maintained at 155–165° C. and 135 psia after purging 5 times with 200 psia $N_2$.

After 2.5 hours, the dehydrogenation finishing reaction mixture is continuously withdrawn at a rate of 5.9 g/min and introduced into a cyanomethylation reactor. The cyanomethylation reactor is a 1000 ml, 3-necked, round-bottom flask containing a magnetic stirrer and fitted with an adapter for $N_2$. The flask is in a lethal service facility, and cooled in an ice bath at 2° C. In addition to the 5.9 g/min of effluent from the dehydrogenation finishing reactor, also pumped into the flask are 37% formalin at a rate of 2.6 g/min, and liquid HCN at a rate of 0.9 g/min.

After 1 hour (and the addition of 564 g of reactants), the cyanomethylation reaction mixture is continuously pumped at 9.4 g/min into a cyanomethylation finishing reactor. The cyanomethylation finishing reactor is a 1000 ml, 3-necked, round-bottom flask having a magnetic stirrer and fitted with an adapter for $N_2$. The flask is at ambient temperature.

After 1 hour (and the addition of 564 g of reactants), the cyanomethylation finishing reaction mixture (containing sodium N-cyanomethylglycinate) is continuously pumped at 9.4 g/min to a stripper. The stripper is a Teflon spinning band column operating at 100 mm Hg. The cyanomethylation finishing reactor mixture is introduced at the top of the stripper column. The sodium N-cyanomethylglycinate flows down the spinning column to a 50 ml receiver concurrent with the removal of excess HCN and other volatiles at the top of the column.

Crude aqueous sodium N-cyanomethylglycinate is continuously pumped at 9.4 g/min to a hydrolysis reactor. The hydrolysis reactor is a 5000 ml, 3-necked, round-bottom flask having a magnetic stirrer and fitted with an adapter for the $N_2$ sweep. With the flask at ambient temperature, 40% NaOH is pumped continuously into the stirred hydrolysis reactor at a rate of 2.6 g/min. After 6 hours, the reaction mixture in the hydrolysis reactor is pumped at a rate of 12.0 g/min to a product vessel and analyzed via liquid chromatography to confirm the presence of disodium iminodiacetic acid.

Example 13

Preparation of a Dehydrogenation Catalyst: Displacement Deposition of a Copper Coating onto a Nickel Sponge Support in Presence of Rochelle Salt A mixture was formed by mixing (1) reagent grade $CUSO_4.5H_2O$ (9.82 g, equivalent to 2.5 g Cu) (Mallinckrodt, St. Louis, Mo.), (2) sodium potassium tartrate hydrate (15 g, Rochelle salt) (Aldrich Chemical Co., Milwaukee, Wis.), and (3) deionized water (300 ml). This mixture was added dropwise at room temperature to a mechanically-stirred slurry containing Raney® 3201 molybdenum-promoted nickel sponge (7.57 g) from W. R. Grace & Co., Chattanooga, TN in 50 ml of water. After about 45 minutes, the stirring was discontinued. The supernatant was then decanted after the catalyst settled, and an aqueous solution containing 50% by weight NaOH (approximately 50 ml) was then added to the remaining slurry (this is sometimes described in the art as a "Sullivan exchange").

During this copper deposition, the color of the solution containing the Raney® nickel changed from blue (the blue color stemming from the presence of $Cu^{2+}$ ions) to green (the green color stemming from the presence of nickel ions), thereby evidencing the displacement of nickel with copper. Table 1 shows the UV/V is spectroscopy data at various points over the 45 minute copper deposition. As may be seen, the endpoint of the deposition could be conveniently determined by monitoring the wavelength of maximum absorbance ($\lambda_{max}$) and/or the absorbance of the maximum wavelength, which both stabilize as the endpoint is approached.

TABLE 2

UV/Vis Data Tracking Copper
Uptake by Molybdenum-Promoted Nickel Sponge

| Time (min.) | $\lambda_{max}$ (nm) | Absorbance ($\lambda_{max}$) |
| --- | --- | --- |
| 0.5 | 796 | 2.20 |
| 3 | 796 | 1.18 |
| 9 | 784 | 1.00 |
| 20 | 750 | 0.73 |
| 33 | 740 | 0.46 |
| 45 | 736 | 0.41 |

Example 14
Preparation of a Dehydrogenation Catalyst: Displacement Deposition of a Copper Coating onto a Nickel Sponge Support in Presence of EDTA A mixture was formed by mixing (1) reagent grade $CuSO_4.5H_2O$ (5.89 g, equivalent to 1.5 g Cu) (Mallinckrodt), (2) an aqueous solution containing 50 wt. % NaOH (15.1 g), (3) EDTA (13.80 g) (from Aldrich Chemical Co.), and (4) deionized water (50 ml). This mixture was added dropwise at room temperature over a period of 65 minutes to a mechanically-stirred slurry which had previously been prepared by mixing (1) Raney® 3201 molybdenum-promoted nickel sponge (7.54 g) (from W. R. Grace & Co.) in 50 ml of water, (2) EDTA (20.69 g), (3) an aqueous solution containing 50 wt. % NaOH (22.66 g), and (4) deionized water (500 ml). After about 10 minutes of additional stirring, the supernatant was decanted, and an aqueous solution of 50 wt. % NaOH (50 ml) was added to the remaining slurry.

Example 15
Preparation of a Dehydrogenation Catalyst: Displacement Deposition of a Copper Coating onto a Pre-reduced, un-promoted Nickel Sponge Support An aqueous solution containing 12 wt. % $NaBH_4$ in 14 M NaOH (approximately 21 g) (from Aldrich Chemical Co.) was added to deionized water (200 ml), and then sparged with $N_2$. The resulting solution was then added to Raney® 2800 un-promoted nickel sponge (9.20 g) (from W. R. Grace & Co.) in 50 ml of water, and the resulting mixture was stirred for 35 minutes. The supernatant was subsequently decanted, and deionized water (200 ml) was added to the remaining slurry. This mixture was then mixed with a second mixture which was prepared by mixing Rochelle salt (3.5 g) (from Aldrich Chemical Co.), deionized water (500 ml), and L-tartaric acid (2.1 g) (Aldrich). The L-tartaric acid was used to buffer the solution to a pH of 3. Stirring was resumed, and a nitrogen-sparged mixture containing reagent grade $CuSO_45H_2O$ (7.23 g, equivalent to 1.84 g Cu) (from Mallinckrodt) in 100 ml of water was then added dropwise over 50 minutes. The resulting mixture was stirred for an additional 15 minutes. The supernatant was then decanted, and the catalyst was washed with deionized water (200 ml) before being mixed with an aqueous solution of 50 wt. % NaOH (50 ml).

Example 16
Preparation of a Dehydrogenation Catalyst: Displacement Deposition of a Copper Coating onto an Un-Promoted Nickel Sponge Support Pre-Treated with Acetone A mixture containing Raney® 4200 un-promoted nickel sponge (14.13 g) (from W. R. Grace & Co.) and water (50 ml) was added to a solution of deionized water (75 ml) and acetone (75 ml). The acetone was used to remove hydrogen absorbed in the nickel which leads to undesired rapid plating, thus ensuring that all the copper was deposited by electroless plating. The resulting mixture was stirred under air for an hour, and then mixed with a second mixture that was prepared by mixing (1) reagent grade $CuSO_4.5H_2O$ (3.89 g, equivalent to 0.99 g Cu) (from Mallinckrodt), (2) potassium tartrate (10.0 g), (3) an aqueous solution containing 50 wt. % NaOH (3.13 g), and (4) deionized water (100 ml). Stirring was continued for an additional 10 minutes. The catalyst was then allowed to settle, and the supernatant was decanted. The catalyst was subsequently washed twice with an aqueous solution of 50 wt. % NaOH (50 ml). Afterward, the catalyst was placed into an aqueous solution of 50 wt. % NaOH (36.5 g).

Example 17
Preparation of a Dehydrogenation Catalyst: Electroless Plating of Copper onto a Nickel Sponge Support A mixture containing Raney® 2800 nickel sponge (9.09 g) (from W. R. Grace & Co.) and water (50 ml) was added to deionized water (150 ml) and acetone (150 ml). The resulting mixture was stirred under continuous nitrogen sparging for an hour. Afterward, the supernatant was decanted. A second mixture was prepared by mixing (1) reagent grade $CuSO_4 5H_2O$ (4.99 g, equivalent to 1.34 g Cu) (from Mallinckrodt), (2) EDTA (6.27 g), (3) an aqueous solution containing 50 wt. % NaOH (5.15 g), and (4) deionized water (450 ml). This mixture was sparged with $N_2$ and added to the remaining sponge slurry. Next, sodium hypophosphite ($NaH_2PO_2$) (2.17 g) (from Aldrich Chemical Co.) was added dropwise over an hour while continuously sparging the mixture with $N_2$. The resulting mixture was then stirred for an additional 90 minutes under continuous $N_2$ sparging. The pH rose from 3.4 to 7 during this time, and the UV/V is spectroscopy data showed that 0.85 g of copper was removed from the solution (i.e., 0.85 g of copper was plated onto the surface of the nickel sponge), thereby forming a catalyst containing 8.6% copper. To increase the rate of plating, additional sodium hypophosphite hydrate (1 g) was added, and the stirring was continued for another 30 minutes. Finally, the supernatant was decanted, and replaced with an aqueous solution containing 50 wt. % NaOH (50 ml).

Example 18
Preparation of a Dehydrogenation Catalyst: Electroless Plating of Nickel Sponge with Copper EDTA at an Elevated Temperature Using Sodium Hypophosphite as the Reducing Agent Copper nitrate hemipentahydrate (approximately 5.0 g) (from Aldrich), EDTA (6/3 gpf) (Aldrich), and an aqueous solution of 50 wt % NaOH (5.1 g) were contacted with deionized water (400 ml) in a mechanically stirred beaker wrapped with heating tape. While the mixture was being sparged with $N_2$, sodium hypophosphite hydrate (7 g) was added and the mixture was heated to approximately 60° C. Raney® 2800 (approximately 9.1 g) (from W. R. Grace & Co.) in 50 ml of water was added to the mixture, which, in turn, was stirred for 30 minutes. Afterward, a solution of sodium hypophosphite hydrate (5 g) in deionized water (50 ml) was added slowly over 20 minutes. Stirring was stopped five minutes after the addition of the sodium hypophosphite hydrate. Subsequently, the supernatant was decanted, and 50 wt. % NaOH (50 ml) was added to the catalyst slurry.

Example 19
Preparation of a dehydrogenation Catalyst: Electroless Plating of Nickel Sponge with Copper in a Non-aqueous Solvent in the Presence of Sodium Ethoxide (Reducing Agent) and Ethylene Diamine (Chelator) after a $NaBH_4$ Treatment to Remove Surface Oxides Copper(II) chloride dihydrate (approximately 6.17 g) (from Aldrich), ethylene diamine (4.35 g) (from Aldrich) were substantially dissolved in absolute ethanol (250 ml) giving a purple solution with some suspended solid. Raney® 2800 (approximately 9.20 g) (from W. R. Grace & Co.) was slurried in water (50 ml) and then added to a mechanically stirred mixture of water (100 ml) and 12% $NaBH_4$ in 14M NaOH (12.7 g) (Aldrich). Vigorous hydrogen bubbling occurred over about 3 minutes. After 5 minutes, stirring was discontinued and the supernatant was decanted. Two additions of absolute ethanol (100 ml each) followed by swirling and decanting were conducted to exchange the aqueous to the ethanol solvent. The copper/ethylene diamine suspension was then added, followed by stirring and nitrogen sparging. 21% sodium ethoxide in ethanol (approximately 7.4 g) (from Aldrich) was loaded into a dropping funnel and added dropwise over an hour until the color of the supernatant was pale blue. The supernatant was then decanted and the catalyst was rinsed twice with water (200 ml) to remove residual ethanol and sodium chloride. Afterward, a solution of 50% NaOH (50 ml) was added.

Example 20

Preparation of a Copper/Nickel Sponge Dehydrogenation Catalyst

The purpose of this experiment is to prepare a mixed copper/nickel sponge. Without being bound to any particular theory, Applicants currently believe that copper may plate more evenly on such a sponge (relative to copper plating on a pure nickel sponge) because the copper-rich surface of the mixed copper/nickel sponge has more copper nucleation sites for plating.

The sponge was prepared by displacement of aluminum using copper chloride in a 50/50 (wt/wt) nickel/aluminum alloy in the presence of salt (NaCl) to prevent the re-precipitation of aluminum:

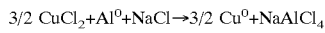

$$3/2\ CuCl_2 + Al^0 + NaCl \rightarrow 3/2\ Cu^0 + NaAlCl_4$$

Although the displacement of aluminum could have alternatively been conducted using, for example, a copper salt of a chelating agent (e.g., the copper salt of EDTA or copper tartrate) and base, such alternative techniques are typically more complicated and slower.

Dry 50/50 (wt/wt) Ni/Al alloy powder (approximately 20.0 g) ("Raney-type alloy," cat. no. 22,165–1, Aldrich) was weighed out and stored under $N_2$. $CuCl_2 \cdot 2H_2O$ (approximately 94.8 g) (from Aldrich) was dissolved in deionized water (300 ml) and then mixed with a solution containing NaCl (64.98 g) in water (200 ml). While mechanically stirring this beaker under $N_2$, ice (approximately 400 g) was added, which reduced the temperature to $-5°$ C. (this did not cause precipitation). The pH of the resulting mixture was 2.1. Next, the Ni/Al alloy was added to the mixture all at once. The mixture was stirred for 30 minutes with continuous $N_2$-sparging during which time the temperature increased to 18° C. and the pH increased to 3.4. The solution was pale green due to acid oxidation of nickel:

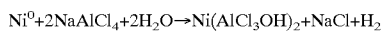

$$Ni^0 + 2NaAlCl_4 + 2H_2O \rightarrow Ni(AlCl_3OH)_2 + NaCl + H_2$$

Stirring was stopped, the supernatant was decanted, and the catalyst was washed with three portions of $N_2$-sparged deionized water (150 ml each). The catalyst was mostly deep copper red, but some black fines were also seen, many of which were lost during the decanting. The catalyst was stirred for 3 hours in a solution containing 50% NaOH (50 g) in deionized water (600 ml) with continuous $N_2$-sparging to complete the hydrolysis of the aluminum. The catalyst color changed to a uniform yellow-brown, indicating that the surface was $Cu_2O$. The catalyst was rinsed with two portions of $N_2$-sparged deionized water (250 ml each) and then stored under water.

Example 21

Preparation of a Dehydrogenation Catalyst: Deposition of a Copper Coating onto the Copper/Nickel Sponge of Example 20 via Displacement Deposition The copper/nickel sponge of Example 15 (approximately 14.7 g) was suspended in an $N_2$-sparged mixture containing 12% $NaBH_4$ in 14 M NaOH (30 g) and water (300 ml). The resulting mixture was stirred for 10 minutes to reduce any oxides on the nickel. The supernatant was then decanted, and the catalyst was rinsed with two portions of water (150 ml each). An $N_2$-sparged solution of copper sulfate pentahydrate (23.57 g) in water (250 ml) was then added to displace nickel on the surface of the sponge with copper. After an hour of stirring, the blue supernatant was decanted and the catalyst was rinsed with water (150 ml) and then solvent-exchanged with 50% NaOH.

Example 22

Preparation of a Copper/Cobalt Sponge Dehydrogenation Catalyst

This example demonstrates the preparation of a copper/cobalt alloy sponge catalyst having a copper to cobalt weight ratio of 3:1.

An alloy (approximately 1 g) containing 52.1 wt. % aluminum, 35.2 wt. % copper, and 12.6 wt. % cobalt, prepared by Grace Davison, was introduced into a Fluitron five-gallon nickel reactor. Subsequently, an aqueous solution containing NaOH (3.07 g) and water (8 L) was added slowly through an addition funnel. To facilitate addition, a slight vacuum was applied to the reactor. The system was purged 3 times with $N_2$, then heated to 160° C. and held at that temperature for 2 hours while stirring. Afterward, the mixture was cooled to 80° C., and then purged 3 more times with $N_2$ before opening the reactor. Four such alloy hydrolysis runs were conducted, ultimately producing a total of 1787 g of activated catalyst. Fines were removed with a 14 mesh screen.

Example 23

Preparation of a Dehydrogenation Catalyst Using Different Amounts of Copper Loading when Coating a Metal Support Three catalysts were prepared by electroless plating of nickel sponge (Raney® 4200, Grace Davison) with copper EDTA using different copper loadings. For each catalyst, a mixture of copper sulfate pentahydrate, 1.1 equivalents of EDTA (based on moles of copper), and 50% NaOH (40 g) in water (400 ml) was prepared and sparged with $N_2$. The nickel sponge was slurried into water (200 g) and a mixture containing 12 wt. % $NaBH_4$ in 14 M NaOH was added dropwise while stirring and $N_2$-sparging. The addition of $NaBH_4$ was stopped when the supernatant was clear and $H_2$ bubbling was observed, i.e., when about 1.3 equivalents of the $NaBH_4$ (based on moles of copper) was added. The amounts of the reagents used are given in Table 3.

TABLE 3

Catalyst Preparation

| Copper loading | Nickel sponge | CuSO$_4$.5H$_2$O | EDTA | NaBH$_4$ add time |
|---|---|---|---|---|
| 10% | 9.19 g in 200 g H$_2$O | 3.61 g | 4.65 g | 45 min |
| 15% | 9.22 g in 200 g H$_2$O | 5.44 g | 7.00 g | 40 min |
| 25% | 9.27 g in 200 g H$_2$O | 9.09 g | 11.71 g | 25 min. |

Example 24
Preparation of a Copper-coated, Copper-Doped Nickel Sponge

This example demonstrates the electrochemical displacement deposition of copper onto a copper-doped nickel sponge catalyst under basic conditions followed by electrochemical displacement deposition of copper under acidic conditions. A copper-doped nickel sponge catalyst (8.96 g), having an initial composition of 78.4% Ni, 8.3% Cu and 13.2% Al (from W. R. Grace of Columbia, MD) was slurried into nitrogen-sparged water (300 ml). A solution of 12% NaBH$_4$ in 14M NaOH was added to the slurry for the removal of surface oxidation. The suspension was stirred for 15 minutes with nitrogen sparging and the catalyst was allowed to settle. The supernatant was decanted and the catalyst was again slurried into nitrogen-sparged water (200 ml).

Electrochemical displacement deposition under basic conditions was begun by adjusting the pH of the catalyst slurry to approximately 7 by the addition of acetic acid. A solution of CuSO$_4$.5H$_2$O (8.80 g, equivalent to 25 wt % Cu with respect to the catalyst), tetrasodium EDTA dihydrate (17.60 g) and water (150 ml) was added to the catalyst slurry. To this mixture, a solution of 2.5N NaOH (56 ml or 4.0 equivalents) in water (50 ml) was added dropwise with continuous stirring and nitrogen sparging. The pH rose from 9.3 to 12.4. A nearly clear supernatant was then decanted.

Immediately after decantation of the previous plating solution, a mixture of 50% gluconic acid (27.6 g or 2.0 equivalents), 2.5N NaOH (5.6 ml or 0.4 equivalents) and water (400 ml) was heated in a 95° C. oil bath and added to the catalyst. A copper salt solution containing CuSO$_4$.5H$_2$O (8.80 g) dissolved in water (100 ml) was the added to the catalyst suspension dropwise over 30 minutes with continuous stirring and nitrogen sparging. During the copper salt addition, the catalyst suspension cooled from 67° C. to 30° C. and the pH of the suspension fell from 3.3 to 2.6. A blue-green supernatant was then decanted and the catalyst was solvent exchanged with nitrogen-sparged 50% NaOH for transfer to a dehydrogenation reactor.

Example 25
Electroless Plating of Nickel Sponge with Copper in a Non-aqueous Solvent This example demonstrates the electroless plating of copper onto a nickel sponge catalyst using a non-aqueous solvent.

Nickel sponge (15 g) was de-watered by sequentially washing and decanting with a 5% aqueous solution of sodium gluconate, THF and toluene. The catalyst was then slurried into a solution containing 10% Cu ion as CuIneodecanoate in toluene (24.8 g), ethylene diamine (1.76 g) and toluene (21 ml).

The catalyst slurry was then charged to a hydrogenation reactor. The reactor gas cap was purged with N$_2$ and H$_2$. The electroless plating was begun by stirring the slurry under 25 to 45 psig of H$_2$ for 3 hours while linearly ramping the temperature inside the reactor from 25° C. to 80° C. The H2 consumed during the reaction was replaced to maintain pressure in the reactor.

After the reaction is complete, the reactor was cooled to room temperature and the gas cap was purged with N$_2$. The supernatant, which had a light tan color, was decanted. The catalyst was then slurried into another copper ion solution identical to that described above and the plating procedure was repeated.

After the second electroless plating run, the reactor was cooled, the gas cap was purged with N$_2$ and the supernatant, which again had a light tan color, was decanted. The catalyst was then washed sequentially with toluene, THF, 1% aqueous NaOH and water.

Example 26
Preparation of a Cu-Doped Ni Sponge Dehydrogenation Catalyst

This example describes the preparation of a Cu-doped Ni sponge catalyst that was supplied by the Davison Division of W. R. Grace and Co. The method of preparation was provided to the assignee hereof for use in describing the catalyst. As further explained herein, this catalyst is useful without further modification in catalyzing the dehydrogenation of a primary alcohol such as diethanolamine. Advantageously, it may also be plated with Cu to produce a modified catalyst having a Cu-containing active phase that is also useful in catalyzing such reactions.

Powdered aluminum, nickel and copper were mixed to provide a mixture containing 50% by weight Al, 45% by weight Ni and 5% by weight Cu. The mixture was placed in a graphite crucible/mold and heated in a furnace under an argon atmosphere to form an alloy. The furnace reached a maximum temperature of 1600° C. over a period of 4 hours and this peak temperature was maintained for an additional 15 minutes. The resulting alloy was then cooled to room temperature under Ar over a 3-hour period.

The alloy was then crushed and ground to powder, and sieved using a 270 mesh U.S. Std. sieve. The powder passing through the 270 mesh sieve was then subsequently activated.

The catalyst activation comprised gradually adding, with stirring, the alloy powder to a vessel containing a 30% by weight solution of NaOH in water. The ratio of alloy powder to NaOH solution was 0.22:1 on a weight basis. The alloy was added to the solution and then digested (further stirred and heated) for a total period of 4 hours and 15 minutes. The temperature of the solution during alloy addition and digestion ranged from about 95° to about 105° C.

After digestion, the catalyst was washed with water by a decant method until the pH of the slurry reached 9. The resulting catalyst had a weight basis composition of 77.0% Ni, 8.9% Cu and 13.8% Al. The average particle size was 23 microns as determined by Malvern light scattering method after 30 seconds ultrasound dispersion.

The above process was repeated using an initial metal mixture of 50% by weight Al, 43% by weight Ni and 7% Cu. The resulting copper-doped nickel sponge had a weight basis composition of 69.5% Ni, 11.2% Cu and 18.9% Al.

Example 27
Preparation of a Zinc-Doped Copper Alloy Sponge Catalyst

This example describes the preparation of a Zn-doped Copper alloy sponge catalyst that was supplied by the Davison Division of W. R. Grace and Co. The method of preparation was provided to the assignee hereof for use in describing the catalyst. As further explained herein, this catalyst is useful without further modification in catalyzing the dehydrogenation of a primary alcohol such as diethanolamine. Advantageously, it may also be plated with Cu to produce a modified catalyst having a Cu-containing active phase that is also useful in catalyzing such reactions.

Powdered aluminum, nickel, zinc and copper were mixed to provide a mixture containing 50% by weight Al, 42.5% by weight Ni, 2.5% by weight Zn and 5% by weight Cu. The mixture was placed in a graphite crucible/mold and heated in a furnace under an argon atmosphere to form an alloy. The furnace reached a maximum temperature of 1000° C. over a period of 4 hours and this peak temperature was maintained for an additional 15 minutes. The resulting alloy was then cooled to room temperature under Ar over a 3-hour period.

The alloy was then crushed and ground to powder, and sieved using a 270 mesh U.S. Std. sieve. The powder passing through the 270 mesh sieve was then subsequently activated.

The catalyst activation comprised gradually adding, with stirring, the alloy powder to a vessel containing a 35% by weight solution of NaOH in water. The ratio of alloy powder to NaOH solution was 0.26:1 on a weight basis. The alloy was added to the solution and then digested (further stirred and heated) for a total period of 4 hours and 45 minutes. The temperature of the solution during alloy addition and digestion ranged from about 95° to about 110° C.

After digestion, the catalyst was washed with water by a decant method until the pH of the slurry reached 9. The resulting catalyst had a weight basis composition of 81.4% Ni, 6.3% Cu, 11.5% Al and 0.4% Zn. The average particle size was 24 microns as determined by Malvern light scattering method after 30 seconds ultrasound dispersion.

The above description of the preferred embodiments and examples are intended only to acquaint others skilled in the art with the invention, its principles, and its practical application, so that others skilled in the art may adapt and apply the invention in its numerous forms, as may be best suited to the requirements of a particular use. The present invention, therefore, is not limited to the above embodiments, and may be variously modified.

With reference to the use of the word(s) "comprise" or "comprises" or "comprising" in the above description and/or in the following claims, applicants note that unless the context requires otherwise, those words are used on the basis and clear understanding that they are to be interpreted inclusively, rather than exclusively, and that applicants intend each of those words to be so interpreted in construing the above description and/or the following claims.

The entire texts of all U.S. Patents and other references cited herein are hereby incorporated by reference into this patent.

We claim:

1. A process for making an iminodiacetic acid compound from a monoethanolamine substrate, the process comprising:
    continuously or intermittently introducing said monoethanolamine substrate into a cyanomethylation reaction zone;
    continuously or intermittently contacting said monoethanolamine substrate with a cyanide source and a formaldehyde source in said cyanomethylation reaction zone to form a cyanomethylation product comprising an N-cyanomethylated monoethanolamine intermediate;
    continuously or intermittently introducing at least a portion of said N-cyanomethylated monoethanolamine intermediate from said cyanomethylation product into a hydrolysis/dehydrogenation reaction zone; and
    continuously or intermittently contacting said N-cyanomethylated monoethanolamine intermediate with a hydroxide source and a metal-containing catalyst in said hydrolysis/dehydrogenation reaction zone to form a hydrolysis/dehydrogenation product comprising said iminodiacetic acid compound,
    wherein said monoethanolamine substrate has the formula:

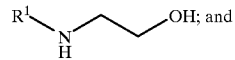

$R^1$ is hydrogen, hydrocarbyl, or substituted hydrocarbyl.

2. A process as set forth in claim 1 wherein $R^1$ is hydrocarbyl.

3. A process as set forth in claim 2, wherein $R^1$ is methyl, ethyl, isopropyl, benzyl, or pentyl.

4. A process as set forth in claim 3, wherein $R^1$ is methyl.

5. A process as set forth in claim 1, wherein $R^1$ is hydrogen.

6. A process as set forth in claim 1, wherein said metal-containing catalyst comprises a metal selected from the group consisting of cadmium, copper, nickel, silver and lead.

7. A process as set forth in claim 1, wherein said metal-containing catalyst comprises copper.

8. A process as set forth in claim 7, wherein said metal-containing catalyst comprises a copper-containing active phase at the surface thereof and a supporting structure that is resistant to deformation under the conditions of the hydrolysis/dehydrogenation reaction.

9. A process as set forth in claim 8, wherein said supporting structure comprises titanium oxide, zirconium oxide, or carbon.

10. A process as set forth in claim 8, wherein said metal-containing catalyst further comprises platinum, palladium, ruthenium, or gold at the surface of said supporting structure.

11. A process as set forth in claim 8 wherein said supporting structure comprises a metal sponge containing at least about 15% by weight non-copper metal and at least about 10% by weight copper.

12. A process as set forth in claim 8 wherein the active phase at the surface of said catalyst comprises at least about 50% by weight copper.

13. A process as set forth in claim 12 wherein said active phase contains less than about 1% by weight of a metal oxide other than cuprous oxide.

14. A process as set forth in claim 12 wherein said active phase contains less than about 1% by weight of cuprous oxide.

15. A process as set forth in claim 12 wherein said active phase contains at least about 1% by weight of a supplemental metal selected from the group consisting of chromium, titanium, niobium, tantalum, zirconium, vanadium, molybdenum, manganese, tungsten, cobalt, nickel, bismuth, tin, antimony, lead, and germanium, and mixtures thereof.

16. A process as set forth in claim 8 wherein said supporting structure comprises a metal containing at least about 10% by weight non-copper metal.

17. A process as set forth in claim 16 wherein said catalyst comprises a metal sponge.

18. A process as set forth in claim 16, wherein said metal support comprises at least about 10% by weight of a non-copper metal selected from the group consisting of nickel, zinc, tin, cobalt and iron, or a combination thereof.

19. A process as set forth in claim 16 wherein said catalyst comprises a surface stratum comprising said active phase, said surface stratum containing between about 0.005 and about 0.5 grams of copper per gram of said supporting structure.

20. A process as set forth in claim 16 wherein said catalyst comprises a metal sponge support having deposited thereon a copper-containing outer stratum.

21. A process as set forth in claim 1, wherein:
said formaldehyde source comprises formalin, paraformaldehyde, or glycolonitrile; and
said cyanide source comprises hydrogen cyanide or a salt thereof, or glycolonitrile.

22. A process as set forth in claim 21 wherein said cyanide source comprises sodium cyanide or potassium cyanide.

23. A process as set forth in claim 21 wherein said formaldehyde source and said cyanide source is glycolonitrile.

24. A process as set forth in claim 1, wherein said hydroxide source comprises an alkali metal hydroxide.

25. A process as set forth in claim 1, wherein said hydroxide source comprises NaOH.

26. A process as set forth in claim 1 wherein said N-cyanomethylated monoethanolamine intermediate is contacted with said hydroxide source and said metal-containing catalyst at a reaction temperature of from about 140° C. to about 190° C.

27. A process as set forth in claim 1, wherein said monoethanolamine substrate comprises 2-aminoethanol, said N-cyanomethylated monoethanolamine intermediate comprises 2-(N-cyanomethylamino)ethanol, and said iminodiacetic acid compound comprises disodium iminodiacetic acid.

28. A process as set forth in claim 1, wherein said process is conducted in a continuous reactor system.

29. A process as set forth in claim 28, wherein said cyanomethylation reaction zone comprises a stirred-tank reactor.

30. A process as set forth in claim 28, wherein said cyanomethylation reaction zone comprises at least two stirred-tank reactors in series.

31. A process as set forth in claim 28, wherein said process further comprises separating hydrogen cyanide and/or water from said N-cyanomethylated monoethanolamine intermediate prior to introducing said N-cyanomethylated monoethanolamine intermediate into said hydrolysis/dehydrogenation reaction zone.

32. A process as set forth in claim 31, wherein said hydrogen cyanide and/or said water are separated from said N-cyanomethylated monoethanolamine intermediate in a stripper.

33. A process as set forth in claim 28, wherein said hydrolysis/dehydrogenation reaction zone comprises a stirred-tank reactor.

34. A process as set forth in claim 28, wherein said hydrolysis/dehydrogenation reaction zone comprises at least two stirred-tank reactors in series.

35. A process as set forth in claim 1, wherein said process further comprises phosphonomethylating said iminodiacetic acid compound to form N-(phosphonomethyl) iminodiacetic acid or a salt thereof.

36. A process as set forth in claim 35, wherein said process further comprises oxidizing said N-(phosphonomethyl)iminodiacetic acid to form N-(phosphonomethyl)glycine or a salt thereof.

37. A process for making an iminodiacetic acid compound from a monoethanolamine substrate, the process comprising:
continuously or intermittently introducing said monoethanolamine substrate into a cyanomethylation reaction zone;
continuously or intermittently contacting said monoethanolamine substrate with a source of formaldehyde and a source of cyanide in said cyanomethylation reaction zone to form a cyanomethylation product comprising a N-cyanomethylated monoethanolamine intermediate;
continuously or intermittently introducing at least a portion of said N-cyanomethylated monoethanolamine intermediate from said cyanomethylation product into a hydrolysis reaction zone;
continuously or intermittently contacting said N-cyanomethylated monoethanolamine intermediate with a hydroxide source in said hydrolysis reaction zone to form a hydrolysis product comprising an N-(2-hydroxyethyl)glycine intermediate;
continuously or intermittently introducing at least a portion of said N-(2-hydroxyethyl)glycine intermediate from said hydrolysis product into a dehydrogenation reaction zone; and
continuously or intermittently contacting said N-(2-hydroxyethyl)glycine intermediate with a metal-containing catalyst in said dehydrogenation reaction zone to form a dehydrogenation product comprising an iminodiacetic acid compound,
wherein said monoethanolamine substrate has the formula:

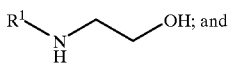

$R^1$ is hydrogen, hydrocarbyl, or substituted hydrocarbyl.

38. A process as set forth in claim 37 wherein $R^1$ is hydrocarbyl.

39. A process as set forth in claim 38, wherein $R^1$ is methyl, ethyl, isopropyl, benzyl, or pentyl.

40. A process as set forth in claim 39, wherein $R^1$ is methyl.

41. A process as set forth in claim 37, wherein $R^1$ is hydrogen.

42. A process as set forth in claim 37, wherein said metal-containing catalyst comprises a metal selected from the group consisting of cadmium, copper, nickel, silver and lead.

43. A process as set forth in claim 37, wherein said metal-containing catalyst comprises copper.

44. A process as set forth in claim 43, wherein said metal-containing catalyst comprises a copper-containing active phase at the surface thereof and a supporting structure that is resistant to deformation under the conditions of the dehydrogenation reaction.

45. A process as set forth in claim 44, wherein said supporting structure comprises titanium oxide, zirconium oxide, or carbon.

46. A process as set forth in claim 43, wherein said metal-containing catalyst further comprises platinum, palladium, ruthenium, or gold at the surface of said supporting structure.

47. A process as set forth in claim 43 wherein said supporting structure comprises a metal sponge containing at least about 15% by weight non-copper metal and at least about 10% by weight copper.

48. A process as set forth in claim 43 wherein the active phase at the surface of said catalyst comprises at least about 50% by weight copper.

49. A process as set forth in claim 48 wherein said active phase contains less than about 1% by weight of a metal oxide other than cuprous oxide.

50. A process as set forth in claim 48 wherein said active phase contains less than about 1% by weight of cuprous oxide.

51. A process as set forth in claim 48 wherein said active phase contains at least about 1% by weight of a supplemental metal selected from the group consisting of chromium, titanium, niobium, tantalum, zirconium, vanadium, molybdenum, manganese, tungsten, cobalt, nickel, bismuth, tin, antimony, lead, and germanium, and mixtures thereof.

52. A process as set forth in claim 43 wherein said supporting structure comprises a metal containing at least about 10% by weight non-copper metal.

53. A process as set forth in claim 52 wherein said catalyst comprises a metal sponge.

54. A process as set forth in claim 52, wherein said metal support comprises at least about 10% by weight of a non-copper metal selected from the group consisting of nickel, zinc, tin, cobalt and iron, or a combination thereof.

55. A process as set forth in claim 52 wherein said catalyst comprises a surface stratum comprising said active phase, said surface stratum containing between about 0.005 and about 0.5 grams of copper per gram of said supporting structure.

56. A process as set forth in claim 52 wherein said catalyst comprises a metal sponge support having deposited thereon a copper-containing outer stratum.

57. A process as set forth in claim 37, wherein:
said formaldehyde source comprises formalin, paraformaldehyde, or glycolonitrile; and
said cyanide source comprises hydrogen cyanide or a salt thereof, or glycolonitrile.

58. A process as set forth in claim 57 wherein said cyanide source comprises sodium cyanide or potassium cyanide.

59. A process as set forth in claim 57 wherein said formaldehyde source and said cyanide source is glycolonitrile.

60. A process as set forth in claim 37, wherein said hydroxide source comprises an alkali metal hydroxide.

61. A process as set forth in claim 37, wherein said hydroxide source comprises NaOH.

62. A process as set forth in claim 37, wherein said monoethanolamine substrate comprises 2-aminoethanol, said N-cyanomethylated monoethanolamine intermediate comprises 2-(N-cyanomethylamino)ethanol, said N-(2-hydroxyethyl)glycine intermediate comprises sodium N-(2-hydroxyethyl)glycinate, and said iminodiacetic acid compound comprises disodium iminodiacetic acid.

63. A process as set forth in claim 37, wherein said process is conducted in a continuous reactor system.

64. A process as set forth in claim 63, wherein said cyanomethylation reaction zone comprises a stirred-tank reactor.

65. A process as set forth in claim 63, wherein said cyanomethylation reaction zone comprises at least two stirred-tank reactors in series.

66. A process as set forth in claim 63, wherein said process further comprises separating hydrogen cyanide and/or water from said N-cyanomethylated monoethanolamine intermediate prior to introducing said N-cyanomethylated monoethanolamine intermediate into said hydrolysis reaction zone.

67. A process as set forth in claim 66, wherein said hydrogen cyanide and/or said water are separated from said N-cyanomethylated monoethanolamine intermediate in a stripper.

68. A process as set forth in claim 66, wherein at least a portion of said hydrogen cyanide separated from said N-cyanomethylated aminoethanol intermediate is recycled back to the cyanomethylation reaction zone for contacting said monoethanolamine substrate.

69. A process as set forth in claim 63, wherein said process further comprises separating ammonia from said N-(2-hydroxyethyl)glycine intermediate prior to introducing said N-(2-hydroxyethyl)glycine intermediate into said dehydrogenation reaction zone.

70. A process as set forth in claim 63, wherein said dehydrogenation reaction zone comprises a stirred-tank reactor.

71. A process as set forth in claim 63, wherein said dehydrogenation reaction zone comprises at least two stirred-tank reactors in series.

72. A process as set forth in claim 37, wherein said process further comprises phosphonomethylating said iminodiacetic acid compound to form N-(phosphonomethyl) iminodiacetic acid or a salt thereof.

73. A process as set forth in claim 72, wherein said process further comprises oxidizing said N-(phosphonomethyl)iminodiacetic acid to form N-(phosphonomethyl)glycine or a salt thereof.

74. A process for making disodium iminodiacetic acid from 2-aminoethanol, the process comprising:
continuously or intermittently introducing said 2-aminoethanol into a cyanomethylation reaction zone;
continuously or intermittently contacting said 2-aminoethanol with a cyanide source and a formaldehyde source in said cyanomethylation reaction zone to form a cyanomethylation product comprising 2-(N-cyanomethylamino)ethanol;
continuously or intermittently introducing at least a portion of said 2-(N-cyanomethylamino)ethanol from said cyanomethylation product into a hydrolysis/ dehydrogenation reaction zone; and
continuously or intermittently contacting said 2-(N-cyanomethylamino)ethanol with sodium hydroxide and a metal-containing catalyst in said hydrolysis/ dehydrogenation reaction zone to form a hydrolysis/ dehydrogenation product comprising disodium iminodiacetic acid.

75. A process as set forth in claim 74, wherein said metal-containing catalyst comprises a metal selected from the group consisting of cadmium, copper, nickel, silver and lead.

76. A process as set forth in claim 74, wherein said metal-containing catalyst comprises copper.

77. A process as set forth in claim 76, wherein said metal-containing catalyst comprises a copper-containing active phase at the surface thereof and a supporting structure that is resistant to deformation under the conditions of the hydrolysis/dehydrogenation reaction.

78. A process as set forth in claim 77 wherein said supporting structure comprises a metal sponge containing at least about 15% by weight non-copper metal and at least about 10% by weight copper.

79. A process as set forth in claim 77 wherein the active phase at the surface of said catalyst comprises at least about 50% by weight copper.

80. A process as set forth in claim 79 wherein said active phase contains less than about 1% by weight of a metal oxide other than cuprous oxide.

81. A process as set forth in claim 79 wherein said active phase contains less than about 1% by weight of cuprous oxide.

82. A process as set forth in claim 79 wherein said active phase contains at least about 1% by weight of a supplemental metal selected from the group consisting of chromium, titanium, niobium, tantalum, zirconium, vanadium, molybdenum, manganese, tungsten, cobalt, nickel, bismuth, tin, antimony, lead, and germanium, and mixtures thereof.

83. A process as set forth in claim 77 wherein said supporting structure comprises a metal containing at least about 10% by weight non-copper metal.

84. A process as set forth in claim 83 wherein said catalyst comprises a metal sponge.

85. A process as set forth in claim 83, wherein said metal support comprises at least about 10% by weight of a non-copper metal selected from the group consisting of nickel, zinc, tin, cobalt and iron, or a combination thereof.

86. A process as set forth in claim 83 wherein said catalyst comprises a surface stratum comprising said active phase, said surface stratum containing between about 0.005 and about 0.5 grams of copper per gram of said supporting structure.

87. A process as set forth in claim 83 wherein said catalyst comprises a metal sponge support having deposited thereon a copper-containing outer stratum.

88. A process as set forth in claim 74, wherein:
said formaldehyde source comprises formalin, paraformaldehyde, or glycolonitrile; and
said cyanide source comprises hydrogen cyanide or a salt thereof, or glycolonitrile.

89. A process as set forth in claim 88 wherein said cyanide source comprises sodium cyanide or potassium cyanide.

90. A process as set forth in claim 88 wherein said formaldehyde source and said cyanide source is glycolonitrile.

91. A process as set forth in claim 74 wherein said 2-(N-cyanomethylamino)ethanol is contacted with said hydroxide source and said metal-containing catalyst at a reaction temperature of from about 140° C. to about 190° C.

92. A process as set forth in claim 74, wherein said process is conducted in a continuous reactor system.

93. A process as set forth in claim 92, wherein said cyanomethylation reaction zone comprises a stirred-tank reactor.

94. A process as set forth in claim 92, wherein said cyanomethylation reaction zone comprises at least two stirred-tank reactors in series.

95. A process as set forth in claim 92, wherein said process further comprises separating hydrogen cyanide and/or water from said 2-(N-cyanomethylamino)ethanol prior to introducing said 2-(N-cyanomethylamino)ethanol into said hydrolysis/dehydrogenation reaction zone.

96. A process as set forth in claim 95, wherein said hydrogen cyanide and/or said water are separated from said 2-(N-cyanomethyamino)ethanol in a stripper.

97. A process as set forth in claim 92, wherein said hydrolysis/dehydrogenation reaction zone comprises a stirred-tank reactor.

98. A process as set forth in claim 92, wherein said hydrolysis/dehydrogenation reaction zone comprises at least two stirred-tank reactors in series.

99. A process as set forth in claim 79, wherein said process further comprises phosphonomethylating said disodium iminodiacetic acid to form N-(phosphonomethyl) iminodiacetic acid or a salt thereof.

100. A process as set forth in claim 99, wherein said process further comprises oxidizing said N-(phosphonomethyl)iminodiacetic acid to form N-(phosphonomethyl)glycine or a salt thereof.

101. A process for making disodium iminodiacetic acid from 2-aminoethanol, the process comprising:
continuously or intermittently introducing said 2-aminoethanol into a cyanomethylation reaction zone;
continuously or intermittently contacting said 2-aminoethanol with a source of cyanide and a source of formaldehyde in said cyanomethylation reaction zone to form a cyanomethylation product comprising 2-(N-cyanomethylamino)ethanol;
continuously or intermittently introducing at least a portion of said 2-(N-cyanomethylamino)ethanol from said cyanomethylation product into a hydrolysis reaction zone;
continuously or intermittently contacting said 2-(N-cyanomethylamino)ethanol with sodium hydroxide in said hydrolysis reaction zone to form a hydrolysis product comprising sodium N-(2-hydroxyethyl) glycinate;
continuously or intermittently introducing at least a portion of said sodium N-(2-hydroxyethyl)glycinate from said hydrolysis product into a dehydrogenation reaction zone; and
continuously or intermittently contacting said sodium N-(2-hydroxyethyl)glycinate with a metal-containing catalyst in said dehydrogenation reaction zone to form a dehydrogenation product comprising disodium iminodiacetic acid.

102. A process as set forth in claim 101, wherein said metal-containing catalyst comprises a metal selected from the group consisting of cadmium, copper, nickel, silver and lead.

103. A process as set forth in claim 101, wherein said metal-containing catalyst comprises copper.

104. A process as set forth in claim 103, wherein said metal-containing catalyst comprises a copper-containing active phase at the surface thereof and a supporting structure that is resistant to deformation under the conditions of the dehydrogenation reaction.

105. A process as set forth in claim 104 wherein said supporting structure comprises a metal sponge containing at least about 15% by weight non-copper metal and at least about 10% by weight copper.

106. A process as set forth in claim 104 wherein the active phase at the surface of said catalyst comprises at least about 50% by weight copper.

107. A process as set forth in claim 106 wherein said active phase contains less than about 1% by weight of a metal oxide other than cuprous oxide.

108. A process as set forth in claim 106 wherein said active phase contains less than about 1% by weight of cuprous oxide.

109. A process as set forth in claim 106 wherein said active phase contains at least about 1% by weight of a supplemental metal selected from the group consisting of chromium, titanium, niobium, tantalum, zirconium, vanadium, molybdenum, manganese, tungsten, cobalt, nickel, bismuth, tin, antimony, lead, and germanium, and mixtures thereof.

110. A process as set forth in claim 104 wherein said supporting structure comprises a metal containing at least about 10% by weight non-copper metal.

111. A process as set forth in claim 110 wherein said catalyst comprises a metal sponge.

112. A process as set forth in claim 110, wherein said metal support comprises at least about 10% by weight of a non-copper metal selected from the group consisting of nickel, zinc, tin, cobalt and iron, or a combination thereof.

113. A process as set forth in claim 110 wherein said catalyst comprises a surface stratum comprising said active phase, said surface stratum containing between about 0.005 and about 0.5 grams of copper per gram of said supporting structure.

114. A process as set forth in claim 110 wherein said catalyst comprises a metal sponge support having deposited thereon a copper-containing outer stratum.

115. A process as set forth in claim 101, wherein:
said formaldehyde source comprises formalin, paraformaldehyde, or glycolonitrile; and
said cyanide source comprises hydrogen cyanide or a salt thereof, or glycolonitrile.

116. A process as set forth in claim 115 wherein said cyanide source comprises sodium cyanide or potassium cyanide.

117. A process as set forth in claim 115 wherein said formaldehyde source and said cyanide source is glycolonitrile.

118. A process as set forth in claim 101, wherein said process is conducted in a continuous reactor system.

119. A process as set forth in claim 118, wherein said cyanomethylation reaction zone comprises a stirred-tank reactor.

120. A process as set forth in claim 118, wherein said cyanomethylation reaction zone comprises at least two stirred-tank reactors in series.

121. A process as set forth in claim 119, wherein said process further comprises separating hydrogen cyanide and/or water from said 2-(N-cyanomethylamino)ethanol prior to introducing said 2-(N-cyanomethylamino)ethanol into said hydrolysis reaction zone.

122. A process as set forth in claim 121, wherein said hydrogen cyanide and/or said water are separated from said 2-(N-cyanomethylamino)ethanol in a stripper.

123. A process as set forth in claim 121, wherein at least a portion of said hydrogen cyanide separated from said 2-(N-cyanomethylamino)ethanol is recycled back to said cyanomethylation reaction zone for contacting said 2-aminoethanol.

124. A process as set forth in claim 118, wherein said process further comprises separating ammonia from said sodium N-(2-hydroxyethyl)glycinate prior to introducing said sodium N-(2-hydroxyethyl)glycinate into said dehydrogenation reaction zone.

125. A process as set forth in claim 118, wherein said dehydrogenation reaction zone comprises a stirred-tank reactor.

126. A process as set forth in claim 118, wherein said dehydrogenation reaction zone comprises at least two stirred-tank reactors in series.

127. A process as set forth in claim 101, wherein said process further comprises phosphonomethylating said disodium iminodiacetic acid to form N-(phosphonomethyl) iminodiacetic acid or a salt thereof.

128. A process as set forth in claim 127, wherein said process further comprises oxidizing said N-(phosphonomethyl)iminodiacetic acid to form N-(phosphonomethyl)glycine or a salt thereof.

* * * * *